(12) United States Patent
Buesseler et al.

(10) Patent No.: US 12,064,228 B2
(45) Date of Patent: *Aug. 20, 2024

(54) SYSTEM AND APPARATUS FOR DETECTING CATHETERS RELATIVE TO INTRODUCERS

(71) Applicant: St. Jude Medical, Cardiology Division, Inc., St. Paul, MI (US)

(72) Inventors: Ryan K. Buesseler, Bristow, VA (US); Troy T. Tegg, Elk River, MN (US); Kevin Edmunds, Ham Lake, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/700,422

(22) Filed: Mar. 21, 2022

(65) Prior Publication Data

US 2022/0313107 A1 Oct. 6, 2022

Related U.S. Application Data

(63) Continuation of application No. 15/896,055, filed on Feb. 13, 2018, now Pat. No. 11,304,622.

(Continued)

(51) Int. Cl.
*A61B 5/06* (2006.01)
*A61B 5/00* (2006.01)
(Continued)

(52) U.S. Cl.
CPC .............. *A61B 5/062* (2013.01); *A61B 5/063* (2013.01); *A61B 5/065* (2013.01); *A61B 5/287* (2021.01);
(Continued)

(58) Field of Classification Search
CPC ......... A61B 5/062; A61B 5/063; A61B 5/065; A61B 5/287; A61B 5/6852; A61B 8/12;
(Continued)

(56) References Cited

U.S. PATENT DOCUMENTS 7,263,397 B2 8/2007 Hauck et al.
11,304,622 B2 * 4/2022 Buesseler .......... A61B 18/1492
(Continued)

*Primary Examiner* — Sean D Mattson
(74) *Attorney, Agent, or Firm* — Billion & Armitage

(57) ABSTRACT

An apparatus for detecting relative positioning of medical devices located within a human body, the apparatus comprising an inner elongate member comprising a plurality of electrodes and a first sensor member, where the first sensor member is located a known distance from each of the plurality of electrodes, and an outer elongate member comprising a first sensor, and an outer sensor member located between the first sensor and an inner wall of the outer elongate member, where the inner elongate member is configured to move within the outer elongate member and the first sensor is configured to sense a signal generated by movement of the inner elongate member relative to the outer elongate member, and a position detection module including an electronic control unit configured to detect a position of the first sensor member relative to the first sensor based on the signal.

11 Claims, 8 Drawing Sheets

Related U.S. Application Data

(60) Provisional application No. 62/458,635, filed on Feb. 14, 2017.

(51) Int. Cl.

| | | |
|---|---|---|
| *A61B 5/287* | (2021.01) | |
| *A61B 8/12* | (2006.01) | |
| *A61B 18/14* | (2006.01) | |
| *A61M 25/01* | (2006.01) | |
| *A61B 18/00* | (2006.01) | |
| *A61B 18/02* | (2006.01) | |
| *A61B 34/20* | (2016.01) | |
| *A61B 90/00* | (2016.01) | |

(52) U.S. Cl.
CPC .............. *A61B 5/6852* (2013.01); *A61B 8/12* (2013.01); *A61B 18/1492* (2013.01); *A61M 25/0127* (2013.01); *A61B 2018/00577* (2013.01); *A61B 2018/0212* (2013.01); *A61B 2034/2051* (2016.02); *A61B 2090/061* (2016.02); *A61B 2218/002* (2013.01); *A61M 2025/0166* (2013.01)

(58) Field of Classification Search
CPC ...... A61B 18/1492; A61B 2018/00577; A61B 2018/0212; A61B 2034/2051; A61B 2034/2053; A61B 2090/061; A61B 2218/002; A61M 25/0127; A61M 2025/0166

See application file for complete search history.

(56) References Cited

U.S. PATENT DOCUMENTS

| | | | |
|---|---|---|---|
| 2008/0140006 A1* | 6/2008 | Eskuri | A61B 5/6848 604/117 |
| 2008/0146942 A1 | 6/2008 | Dala-Krishna | |
| 2009/0262979 A1 | 10/2009 | Markowitz et al. | |
| 2010/0036238 A1* | 2/2010 | Neidert | A61B 5/06 600/424 |
| 2011/0066029 A1 | 3/2011 | Lyu et al. | |
| 2013/0206258 A1 | 8/2013 | Duboy et al. | |
| 2013/0303886 A1 | 11/2013 | Ludwin et al. | |
| 2014/0187905 A1* | 7/2014 | Olson | A61M 5/142 600/409 |
| 2014/0275955 A1* | 9/2014 | Crawford | A61B 17/1671 600/409 |
| 2014/0275991 A1* | 9/2014 | Potter | A61B 5/063 600/424 |
| 2015/0011874 A1* | 1/2015 | Amoako-Tuffour | A61M 31/002 604/503 |
| 2017/0172455 A1 | 6/2017 | Pressman et al. | |
| 2017/0325895 A1 | 11/2017 | Krimsky | |
| 2017/0347913 A1* | 12/2017 | Isaacson | A61M 25/0127 |

* cited by examiner

SYSTEM AND APPARATUS FOR DETECTING CATHETERS RELATIVE TO INTRODUCERS

CROSS-REFERENCE TO RELATED APPLICATIONS

This application is a continuation of application Ser. No. 15/896,055, filed 13 Feb. 2018, which claims the benefit of U.S. provisional application No. 62/458,635, filed 14 Feb. 2017, both of which are hereby incorporated by reference as though fully set forth herein.

BACKGROUND a. Field

This disclosure relates to systems and apparatuses for detecting a position of a medical device. In particular, the instant disclosure relates to using a magnetic field to detect the location of a catheter relative to an introducer.

b. Background Art

Electrophysiology catheters are used in a variety of diagnostic and/or therapeutic medical procedures to correct conditions such as atrial arrhythmia, including for example, ectopic atrial tachycardia, atrial fibrillation, and atrial flutter. Arrhythmia can create a variety of dangerous conditions including irregular heart rates, loss of synchronous atrio-ventricular contractions and stasis of blood flow which can lead to a variety of ailments and even death.

Typically in a procedure, a catheter is manipulated through a patient's vasculature to, for example, a patient's heart, and carries one or more electrodes which may be used for mapping, ablation, diagnosis, or other treatments. Once at the intended site, treatment may include radio frequency (RF) ablation, cryoablation, lasers, chemicals, high-intensity focused ultrasound, etc. An ablation catheter imparts such ablative energy to cardiac tissue to create a lesion in the cardiac tissue. This lesion disrupts undesirable electrical pathways and thereby limits or prevents stray electrical signals that lead to arrhythmias. As readily apparent, such treatment requires precise control of the catheter during manipulation to and at the treatment site, which can invariably be a function of a user's skill level.

To position a catheter at a desired site within the body, some type of navigation may be used, such as using mechanical steering features incorporated into the catheter (or an introducer). In some examples, medical personnel may manually manipulate and/or operate the catheter using the mechanical steering features.

In order to facilitate the advancement of catheters through a patient's vasculature, a navigating system may be used. Such navigating systems may include, for example, electric-field-based positioning and navigating systems that are able to determine the position and orientation of the catheter (and similar devices) within the body. In such electric-field-based positioning and navigating systems, it can be important to know when electrodes on the catheter are shielded inside of a sheath or introducer that is being used to position the catheter a desired location.

The foregoing discussion is intended only to illustrate the present field and should not be taken as disavowal of claim scope.

BRIEF SUMMARY

The instant disclosure, in at least one embodiment, comprises an apparatus for detecting relative positioning of medical devices located within a human body, the apparatus comprising an inner elongate member comprising a plurality of electrodes and a first sensor member, where the first sensor member is located a known distance from each of the plurality of electrodes, and an outer elongate member that comprises a first sensor and an outer sensor member located between the first sensor and an inner wall of the outer elongate member, where the inner elongate member is configured to move within the outer elongate member and the first sensor is configured to sense a signal generated by movement of the inner elongate member. The apparatus also comprises a position detection module including an electronic control unit configured to detect a position of the first member relative to the first sensor based on the signal.

In another embodiment, an apparatus for detecting a relative position of a medical devices located within in a human body comprises an inner elongate member where the inner elongate member comprises a plurality of electrodes and a first sensor member, where the first sensor member is located a known distance from each of the plurality of electrodes, and an outer elongate member comprising a second sensor member where the inner elongate member is configured to move within the outer elongate member and the second sensor member is configured to sense a signal generated by movement of the inner elongate member relative to the outer elongate member. The apparatus further comprises a position detection module including an electronic control unit configured to detect a position of the first sensor device relative to the first sensor based on the signal.

In another embodiment, a system comprises a catheter, wherein the catheter comprises a first sensor member and a plurality of electrodes and the location of the first sensor member is known in relation to the plurality of electrodes. The system also comprises an introducer, where the introducer comprises a sensor where the sensor is adapted configured to sense the first sensor member and configured to measure a first signal indicative of a proximity of the first sensor member to the sensor, and an outer sensor member, where the outer sensor member is located between the sensor and an inner wall of the introducer, where the catheter is configured to move within the introducer. The system further comprises an electronic control unit electrically coupled to the sensor and operable to (A) measure the first signal from the sensor, wherein the first signal varies based on a position of the first sensor member in relation to the sensor and the outer sensor member, (B) analyze the first signal to determine a relative position of the catheter within the introducer based on the location of the first sensor member, and (C) generate a relative position information for the catheter within the introducer using the analysis of the first signal.

In yet another embodiment, a system comprises an introducer, where the introducer comprises a sensor configured to measure a first signal indicative of a proximity of a plurality of electrodes on a catheter to the sensor and an outer sensor member located between the sensor and an inner wall of the introducer, the catheter configured to move within the introducer, and an electronic control unit electrically coupled to the sensor where the electronic control unit is operable to (A) measure the first signal from the sensor, wherein the signal varies based on a position of the plurality of electrodes on the catheter in relation to the sensor and the outer sensor member, (B) analyze the first signal to determine a relative position of the catheter within the introducer based on the location of the plurality of electrodes, and (C) generate a relative position information for the catheter within the introducer using the analysis of the first signal.

DETAILED DESCRIPTION OF EMBODIMENTS

Figure 1:
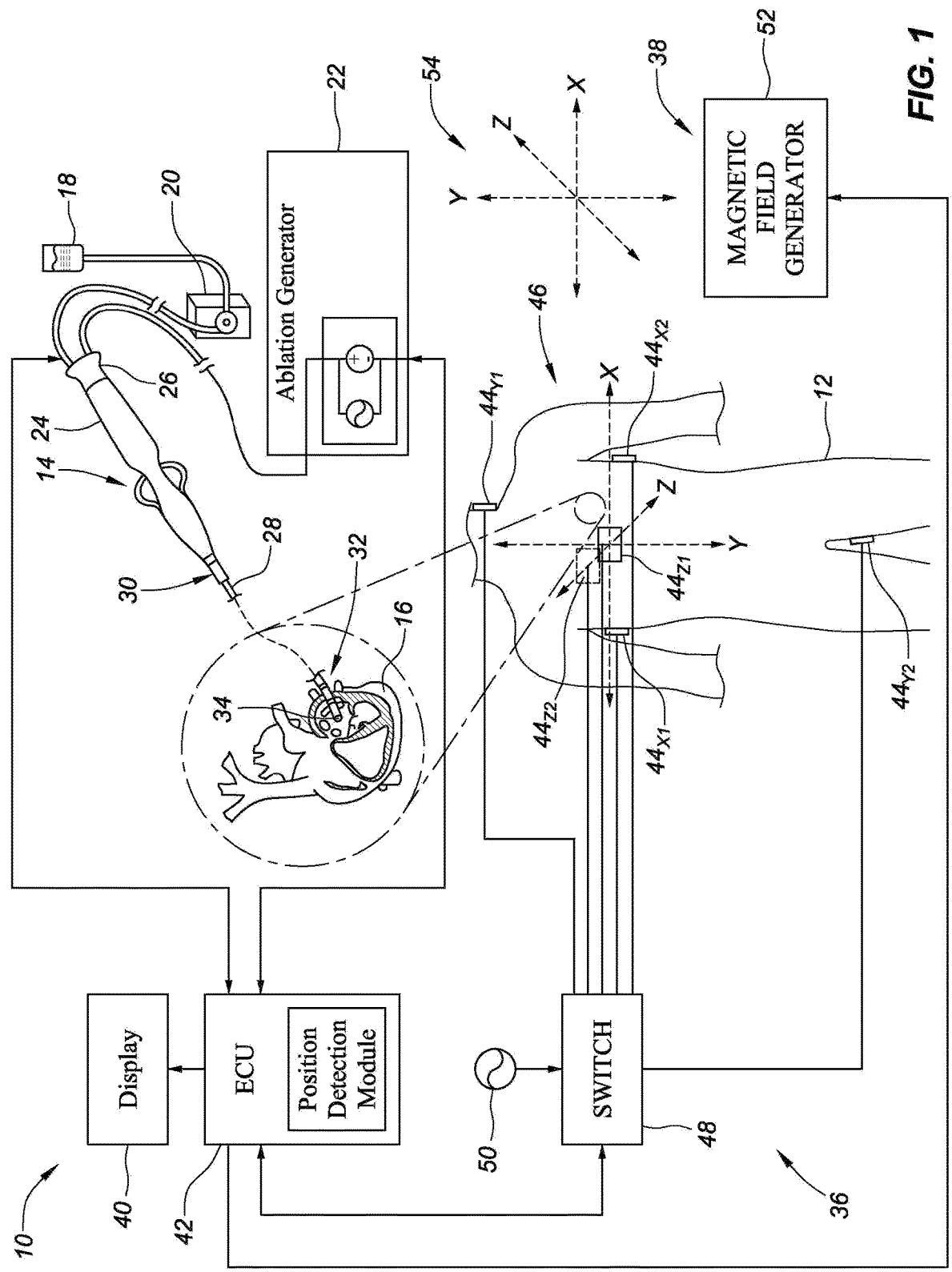
FIG. 1 is a system diagram showing a medical device and a medical positioning system, in accordance with embodiments of the present disclosure.

Referring now to the figures, in which like reference numerals refer to the same or similar features in the various views, FIG. 1 illustrates one embodiment of a system 10 for navigating a medical device within a body 12. In the illustrated embodiment, the medical device comprises a catheter 14 that is shown schematically entering a heart that has been exploded away from the body 12. The catheter 14, in this embodiment, is depicted as an irrigated radiofrequency (RF) ablation catheter for use in the treatment of cardiac tissue 16 in the body 12. It should be understood, however, that the system 10 may find application in connection with a wide variety of medical devices used within the body 12 for diagnosis or treatment. For example, the system 10 may be used to navigate an electrophysiological mapping catheter, an intracardiac echocardiography (ICE) catheter, or an ablation catheter using a different type of ablation energy (e.g., cryoablation, ultrasound, etc.). Further, it should be understood that the system 10 may be used to navigate medical devices used in the diagnosis or treatment of portions of the body 12 other than cardiac tissue 16.

Further description of the systems and components are contained in U.S. patent application Ser. No. 13/839,963 filed on 15 Mar. 2013, which is hereby incorporated by reference in its entirety as though fully set forth herein.

Referring still to FIG. 1, the ablation catheter 14 is connected to a fluid source 18 for delivering a biocompatible irrigation fluid such as saline through a pump 20, which may comprise, for example, a fixed rate roller pump or variable volume syringe pump with a gravity feed supply from fluid source 18 as shown. The catheter 14 is also electrically connected to an ablation generator 22 for delivery of RF energy. The catheter 14 may include a handle 24; a cable connector or interface 26 at a proximal end of the handle 24; and a shaft 28 having a proximal end 30, a distal end 32, and one or more electrodes 34. The connector 26 provides mechanical, fluid, and electrical connections for conduits or cables extending from the pump 20 and the ablation generator 22. The catheter 14 may also include other conventional components not illustrated herein such as a temperature sensor, additional electrodes, and corresponding conductors or leads.

The handle 24 provides a location for the physician to hold the catheter 14 and may further provide means for steering or guiding the shaft 28 within the body 12. For example, the handle 24 may include means to change the length of one or more pull wires extending through the catheter 14 from the handle 24 to the distal end 32 of shaft 28. The construction of the handle 24 may vary.

The shaft 28 may be made from conventional materials such as polyurethane and may define one or more lumens configured to house and/or transport electrical conductors, fluids, or surgical tools. The shaft 28 may be introduced into a blood vessel or other structure within the body 12 through a conventional introducer. The shaft 28 may then be steered or guided through the body 12 to a desired location such as the tissue 16 using guide wires or pull wires or other means known in the art including remote control guidance systems. The shaft 28 may also permit transport, delivery, and/or removal of fluids (including irrigation fluids and bodily fluids), medicines, and/or surgical tools or instruments. It should be noted that any number of methods can be used to introduce the shaft 28 to areas within the body 12. This can include introducers, sheaths, guide sheaths, guide members, guidewires, or other similar devices. For ease of discussion, the term introducer will be used throughout.

The system 10 may include an electric-field-based positioning system 36, a magnetic-field-based positioning system 38, a display 40, and an electronic control unit (ECU) 42 (e.g., a processor). Each of the exemplary system components is described further below.

The electric-field-based positioning system 36 and the magnetic-field-based positioning system 38 are provided to determine the position and orientation of the catheter 14 and similar devices within the body 12. The position and orientation of the catheter 14 and similar devices within the body 12 can be determined by the system 36 and/or the system 38. The system 36 may comprise, for example, the EnSite™ NavX™ system sold by St. Jude Medical, Inc. of St. Paul, Minnesota, and described in, for example, U.S. Pat. No. 7,263,397 titled "Method and Apparatus for Catheter Navigation and Location Mapping in the Heart," the entire disclosure of which is hereby incorporated by reference as though fully set forth herein. The systems 36 and 38 may comprise, for example, the EnSite Precision™ system sold by St. Jude Medical, Inc., of St. Paul, Minnesota The system 36 operates based upon the principle that when low amplitude electrical signals are passed through the thorax, the body 12 acts as a voltage divider (or potentiometer or rheostat) such that the electrical potential or field strength measured at one or more electrodes 34 on the catheter 14 may be used to determine the position of the electrodes, and, therefore, of the catheter 14, relative to a pair of external patch electrodes using Ohm's law and the relative location of a reference electrode (e.g., in the coronary sinus).

In the configuration is shown in FIG. 1, the electric-field-based positioning system 36 further includes three pairs of patch electrodes 44, which are provided to generate electrical signals used in determining the position of the catheter 14 within a three-dimensional coordinate system 46. The electrodes 44 may also be used to generate EP data regarding the tissue 16. To create axes-specific electric fields within body 12, the patch electrodes are placed on opposed surfaces of the body 12 (e.g., chest and back, left and right sides of the thorax, and neck and leg) and form generally orthogonal x, y, and z axes. A reference electrode/patch (not shown) is typically placed near the stomach and provides a reference value and acts as the origin of the coordinate system 46 for the navigation system.

In accordance with this exemplary system 36 as depicted in FIG. 1, the patch electrodes include right side patch $44_{X1}$, left side patch $44_{X2}$, neck patch $44_{Y1}$, leg patch $44_{Y2}$, chest patch $44_{Z1}$, and back patch $44_{Z2}$; and each patch electrode is connected to a switch 48 (e.g., a multiplex switch) and a signal generator 50. The patch electrodes $44_{X1}$, $44_{X2}$ are placed along a first (x) axis; the patch electrodes $44_{Y1}$, $44_{X2}$ are placed along a second (y) axis, and the patch electrodes $44_{Z1}$, $44_{Z2}$ are placed along a third (z) axis. Sinusoidal currents are driven through each pair of patch electrodes, and voltage measurements for one or more position sensors (e.g., ring electrodes 34 or a tip electrode located near the distal end 32 of catheter shaft 28) associated with the catheter 14 are obtained. The measured voltages are a function of the distance of the position sensors from the patch electrodes. The measured voltages are compared to the potential at the reference electrode and a position of the position sensors within the coordinate system 46 of the navigation system is determined.

The magnetic-field-based positioning system 38 in this exemplary embodiment employs magnetic fields to detect the position and orientation of the catheter 14 within the body 12. The system 38 may include the GMPS system made available by MediGuide, Ltd. and generally shown and described in, for example, U.S. Pat. No. 7,386,339 titled "Medical Imaging and Navigation System," the entire disclosure of which is hereby incorporated by reference as though fully set forth herein. In such a system, a magnetic field generator 52 may be employed having three orthogonally arranged coils (not shown) to create a magnetic field within the body 12 and to control the strength, orientation, and frequency of the field. The magnetic field generator 52 may be located above or below the patient (e.g., under a patient table) or in another appropriate location. Magnetic fields are generated by the coils and current or voltage measurements for one or more position sensors (not shown) associated with the catheter 14 are obtained. The measured currents or voltages are proportional to the distance of the sensors from the coils, thereby allowing determination of a position of the sensors within a coordinate system 54 of system 38.

The display 40 is provided to convey information to a physician to assist in diagnosis and treatment. The display 40 may comprise one or more conventional computer monitors or other display devices. The display 40 may present a graphical user interface (GUI) to the physician. The GUI may include a variety of information including, for example, an image of the geometry of the tissue 16, electrophysiology data associated with the tissue 16, graphs illustrating voltage levels over time for various electrodes 34, and images of the catheter 14 and other medical devices and related information indicative of the position of the catheter 14 and other devices relative to the tissue 16.

The ECU 42 provides a means for controlling the operation of various components of the system 10, including the catheter 14, the ablation generator 22, and magnetic generator 52 of the magnetic-field-based positioning system 38. The ECU 42 may also provide a means for determining the geometry of the tissue 16, electrophysiology characteristics of the tissue 16, and the position and orientation of the catheter 14 relative to tissue 16 and the body 12. The ECU 42 also provides a means for generating display signals used to control the display 40.

As the catheter 14 moves within the body 12, and within the electric field generated by the electric-field-based positioning system 36, the voltage readings from the electrodes 34 change, thereby indicating the location of catheter 14 within the electric field and within the coordinate system 46 established by the system 36. The ring electrodes 34 communicate position signals to ECU 42 through a conventional interface (not shown). In order to avoid introducing undesirable shift or drift into the determined catheter position and orientation based upon readings obtained by the electric-field based positioning system 36, it can be important to know when the catheter electrodes 34 are inside the introducer. In particular, if the catheter electrodes 34 are located inside the introducer, the data coming off of those shielded electrodes may be degraded/compromised.

Figure 2A:
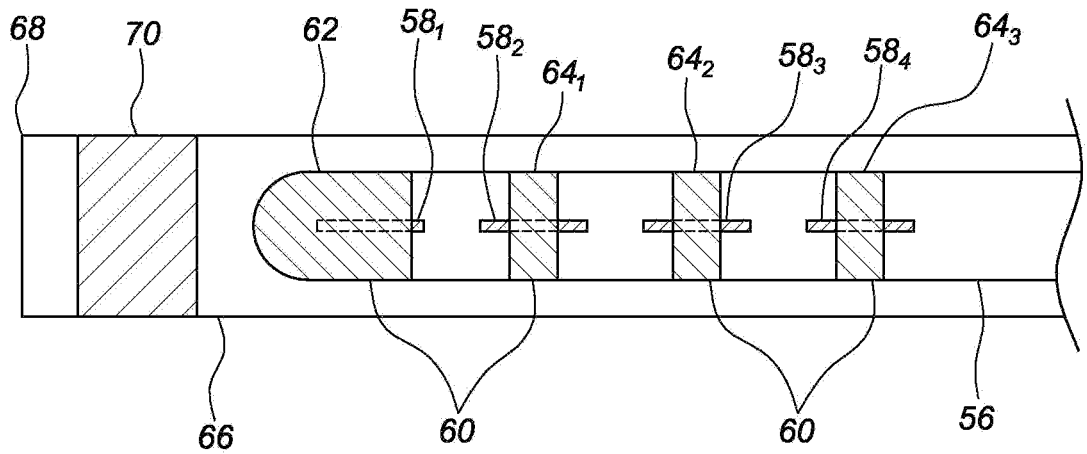
FIG. 2A is a catheter and an introducer, where the catheter includes a plurality of longitudinal sensor members and a plurality of electrodes, where each of the plurality of longitudinal members is the same length, aligned with a longitudinal axis of the catheter, and a known position in relation to a corresponding electrode in a plurality of electrodes positioned on a distal end portion of an introducer and the introducer includes a sensor, in accordance with embodiments of the present disclosure.

FIG. 2A is a catheter and an introducer, where the catheter includes a plurality of longitudinal sensor members and a plurality of electrodes, where each of the plurality of longitudinal members is the same length, aligned with a longitudinal axis of the catheter, and a known position in relation to a corresponding electrode in a plurality of electrodes positioned on a distal end portion of an introducer and the introducer includes a sensor, in accordance with embodiments of the present disclosure. The catheter 56 can include the plurality of longitudinal sensor members 58 and the plurality of electrodes 60. The catheter 56 can be any suitable type of catheter such as an ablation catheter, a diagnostic or mapping catheter, or a combination of both. The catheter 56 can comprise other types of catheters or other devices that are insertable into the body.

The plurality of electrodes 60 can be any suitable type of electrodes. For example, ring electrodes are depicted in the embodiment of FIG. 2A. The plurality of electrodes 60 can include any suitable number of electrodes on the catheter 56. For example, in an embodiment shown in FIG. 2A, the plurality of electrodes 60 includes a tip electrode 62 and three ring electrodes $64_{1-3}$. Embodiments with more or fewer electrodes can also be used.

The plurality of longitudinal sensor members $58_{1-4}$ can be made from a material that facilitates detection by a sensor (e.g., a magnetic sensor, a material with a high magnetic permeability such as Mu metal, Metglas, etc.). The plurality of longitudinal sensor members $58_{1-4}$ can be the same size (e.g., all sensor members have an equal length and width). In some embodiments, the plurality of longitudinal sensor members $58_{1-4}$ can be different shapes of equal size (e.g., circles, ovals, squares, etc.). Each of the plurality of longitudinal sensor members $58_{1-4}$ can be placed so the location of the member is known in relation to the position of a corresponding electrode from the plurality of electrodes 60. For example the middle or center of each corresponding sensor members of the plurality of longitudinal sensor members $58_{1-4}$ can be aligned with the middle or center of a corresponding electrode from the plurality of electrodes 60. In some embodiments, the plurality of longitudinal sensor members $58_{1-4}$ can be rectangular strips with a longer side and a shorter side.

The catheter 56 can be used with an elongate medical device such as an introducer 66, where the introducer 66 can be used to assist with deploying and locating the catheter 56 to a location in a body (e.g., heart tissue). The introducer 66 can have a distal end 68. The introducer 66 can include a sensor 70 (e.g., a coil, a magnetic sensor, etc.) proximate the distal end 68. The sensor 70 can be configured to detect, for example, a proximity of the plurality of longitudinal sensor members 58. The sensor 70 can generate a signal where the signal provides information about the proximity of the plurality of longitudinal sensor members $58_{1-4}$ to the sensor 70 (discussed in greater detail below). For example, as each of the plurality of longitudinal sensor members $58_{1-4}$ moves relative to the sensor 70, the signal can change (e.g., the signal amplitude/strength can increase as a longitudinal sensor member $58_1$ moves closer to the sensor 70 and the signal can decrease as the longitudinal sensor member $58_2$ moves away from to the sensor 70).

In some embodiments, a sensor (e.g., a magnetic sensor) can be used as an encoder. In this embodiment, a catheter can include a sensor member of a high magnetic permeability material (e.g., Mu metal, Metglas, etc.) coupled with and/or proximate to an electrode (e.g., a ring electrode). In other embodiments, a sheath (e.g., introducer 60) can include a sensor (e.g., sensor 70). Exemplary types of sensors can include, for example, a magnetic sensor, a "noisy" sensor (e.g., a sensor with a low signal-to-noise ratio) and other sensors that can detect the sensor member as it passes by the sensor during movement of the catheter in the sheath (e.g. longitudinal and rotational).

Figure 2B:
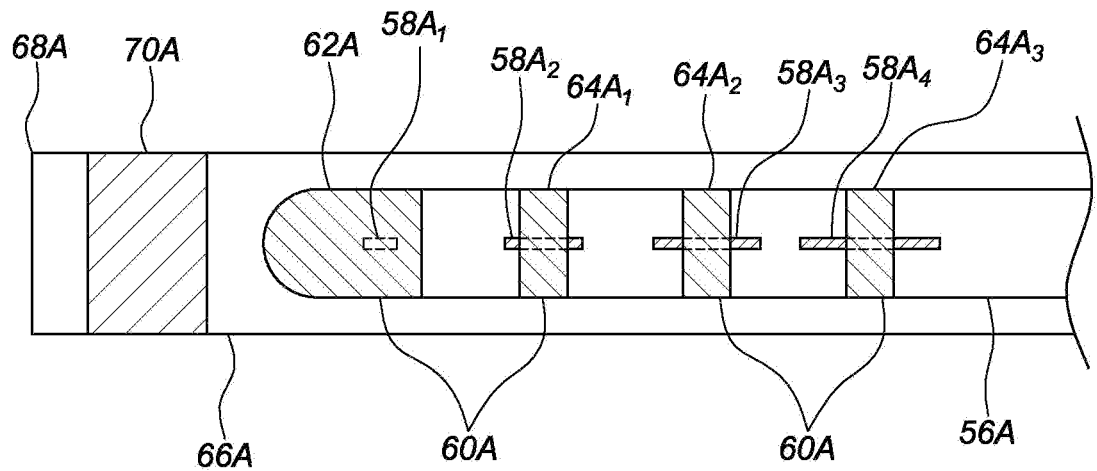
FIG. 2B is a catheter and an introducer, where the catheter includes a plurality of longitudinal sensor members, where the each of the plurality of longitudinal members is a different length and aligned with a longitudinal axis of the catheter, and a known position in relation to a corresponding electrode in a plurality of electrodes positioned on a distal end portion of the catheter, and the introducer includes a sensor, in accordance with embodiments of the present disclosure.

FIG. 2B is a catheter and an introducer, where the catheter includes a plurality of longitudinal sensor members, where the each of the plurality of longitudinal members is a different length and aligned with a longitudinal axis of the catheter, and a known position in relation to a corresponding electrode in a plurality of electrodes positioned on a distal end portion of the catheter, and the introducer includes a sensor, in accordance with embodiments of the present disclosure. The catheter 56A can include the plurality of longitudinal sensor members 58A and the plurality of electrodes 60A.

Similar to FIG. 2A, the catheter 56A in FIG. 2B can be any suitable type of catheter. Also similar to FIG. 2A, the plurality of electrodes 60A can be any suitable type of electrodes (e.g., ring electrodes). The plurality of electrodes 60A can include any suitable number of electrodes on the catheter 56A (e.g., a tip electrode 62A and three ring electrodes $64A_{1-3}$).

Like the embodiment shown in FIG. 2A, the plurality of longitudinal sensor members $58A_{1-4}$ can be made from a material that facilitates detection by a sensor (e.g., a magnetic sensor, a material with a high magnetic permeability such as Mu metal, Metglas, etc.). The plurality of longitudinal sensor members $58A_{1-4}$ can be different sizes (e.g., each sensor member has an different length and width). In some embodiments, the plurality of longitudinal sensor members $58A_{1-4}$ be different sizes of similar shapes (e.g., circles, ovals, squares, etc.). Each of the plurality of longitudinal sensor members $58A_{1-4}$ can be placed so the location of each member is known in relation to the position of a corresponding electrode from the plurality of electrodes 60A. For example, the middle or center of each corresponding sensor member of the plurality of longitudinal sensor members $58A_{1-4}$ can be aligned with the middle or center of a corresponding electrode from the plurality of electrodes 60A.

The catheter 56A can be used with an elongate medical device such as an introducer 66A, where the introducer 66A can be used to assist with deploying and locating the catheter 56A to a location in a body (e.g., heart tissue). The introducer 66A can have a distal end 68A. The introducer 66A can include a sensor 70A (e.g., a coil) proximate the distal end 68A. The sensor 70A can be configured to detect, for example, a proximity of the plurality of longitudinal sensor members 58A. The sensor 70A can generate a signal where the signal provides information about the proximity of the plurality of longitudinal sensor members $58A_{1-4}$ to the sensor 70A (discussed in greater detail below). The information about the proximity of the longitudinal sensor member 58A to the sensor 70A can be used by a position detection module that is part of the ECU to determine a position of the distal end 68A of the catheter 56A in relation to the distal end 68A of the introducer 66A because of the known distances/relationship between the longitudinal sensor member 58A and the plurality of electrodes 60A. In some embodiments, the position detection module can be provided as part of the electric-field-based positioning system 36 and/or the magnetic-field-based positioning system 38 (e.g., as part of the ECU 42).

The position detection module can include, for example, a processor and a memory storing non-transitory computer-readable instructions, as discussed herein (e.g., as part of the ECU 42, or a separate processor and a separate memory, or a combination of the two). The ECU 42 may be programmed with a computer program (e.g., software) encoded on a computer-readable storage medium for assessing for assessing the distances between a plurality of sensor members and one or more sensors. The instructions can be executable to compute, for example, distances between the plurality of longitudinal sensor members 58A and/or a distal end (e.g., the tip electrode 62A) of the catheter 56A and the distal end 68A of the introducer 66A, the rate of change in the distances, or other characteristics related to the position of the distal end of the catheter 56A in relation to the distal end 68A of the introducer 66A. The program can include code for calculating a value responsive to magnitudes of, for example, a voltage between the longitudinal sensor member 58A and the sensor 70A.

Figure 3:
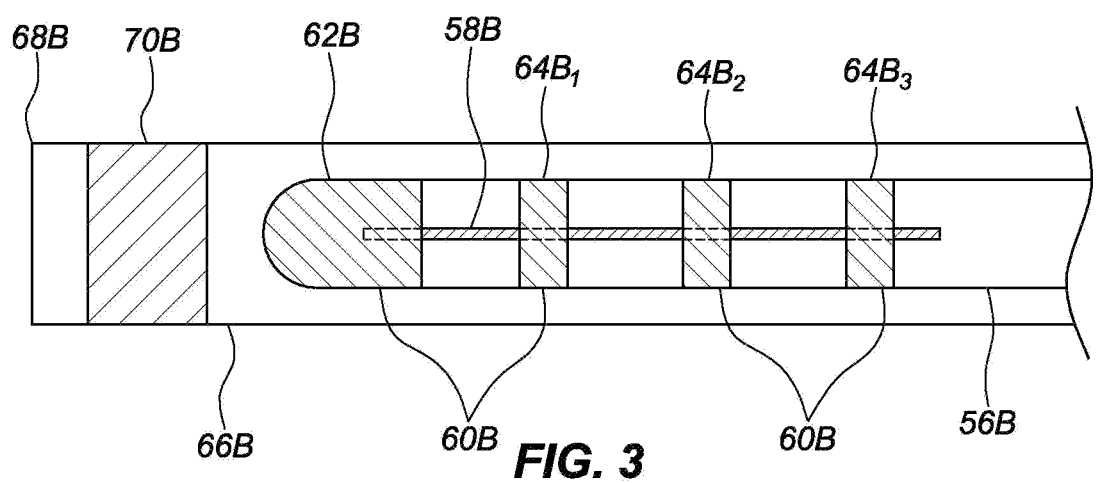
FIG. 3 is a side view of a catheter and an introducer, where the catheter includes a longitudinal sensor member, where the longitudinal member is aligned with a longitudinal axis of the catheter and in a known position in relation to a plurality of electrodes positioned on a distal end portion of the catheter, in accordance with embodiments of the present disclosure.

FIG. 3 is a side view of a catheter and an introducer, where the catheter includes a longitudinal sensor member, where the longitudinal member is aligned with a longitudinal axis of the catheter and in a known position in relation to a plurality of electrodes positioned on a distal end portion of the catheter, in accordance with embodiments of the present disclosure. The catheter 56B can include a longitudinal sensor member $58B_{1-4}$ and a plurality of electrodes 60B.

Similar to FIGS. 2A-B, the catheter 56B in FIG. 3 can be any suitable type of catheter. Also similar to FIGS. 2A-B, the plurality of electrodes 60B can be any suitable type of electrodes (e.g., ring electrodes). The plurality of electrodes 60B can include any suitable number of electrodes on the catheter 56B (e.g., a tip electrode 62B and three ring electrodes $64B_{1-3}$).

The longitudinal sensor member 58B of FIG. 3 can be made from a material that facilitates detection by a sensor (e.g., a magnetic sensor, a material with a high magnetic permeability such as Mu metal, Metglas, etc.). In some embodiments, the longitudinal sensor member 58B can be a different size and/or shape (e.g., a circle, an oval, a square, etc.) including variations in the shape along the longitudinal sensor member 58B (e.g., wider/narrower at the ends, wider/narrower at other areas between the ends, etc.). The longitudinal sensor member 58B can be placed so the location of the member is known in relation to the position of a corresponding electrode from the plurality of electrodes 60B. For example the middle or center of the longitudinal sensor member 58B can be aligned with the middle or center of the plurality of electrodes 60B (e.g., the middle of the longitudinal sensor member 58B can be centered between ring electrodes $64B_1$ and $64B_2$). In some embodiments, the longitudinal sensor member 58B can extend under all or a portion of each or some of the plurality of electrodes 60B (e.g., under a portion of all four exemplary electrodes in FIG. 3 or under a portion of two or three of the electrodes in the four exemplary electrodes in FIG. 3).

The catheter 56B can be used with an elongate medical device such as the introducer 66B, where the introducer 66B can be used to assist with deploying and locating the catheter 56B to a location in a body (e.g., heart tissue). The introducer 66B can have a distal end 68B. The introducer 66B can include the sensor 70B (e.g., a coil) proximate to the distal end 68B. The sensor 70B can be configured to detect, for example, a proximity of the longitudinal sensor member 58B to each of the electrodes (e.g., the plurality of electrodes 60B). The sensor 70B can generate a signal where the signal provides information about the proximity of the plurality of longitudinal sensor members 58B to the sensor 70B (discussed in greater detail below). The information about the proximity of the longitudinal sensor member 58B to the sensor 70B can be used by a position detection module that is part of the ECU to determine a position of the distal end 68B of the catheter 56B in relation to the distal end 68B of the introducer 66B because of the known distances/relationship between the longitudinal sensor member 58B and the plurality of electrodes 60B.

As described above, the position detection module can include, for example, a processor and a memory storing non-transitory computer-readable instructions, as discussed herein (e.g., as part of the ECU 42, or a separate processor and a separate memory, or a combination of the two). The ECU 42 may be programmed with a computer program (e.g., software) encoded on a computer-readable storage medium for assessing the distances between a plurality of longitudinal sensor members and one or more sensors. The instructions can be executable to compute, for example, distances between the longitudinal sensor members 58B and/or a distal end (e.g., the tip electrode 62B) of the catheter 56B and the distal end 68B of the introducer 66B, the rate of change in the distances, or other characteristics related to the position of the distal end of the catheter 56B in relation to the distal end 68B of the introducer 66B. The program can include code for calculating a value responsive to magnitudes of, for example, a voltage between the longitudinal sensor member 58B and the sensor 70B.

Figure 4:
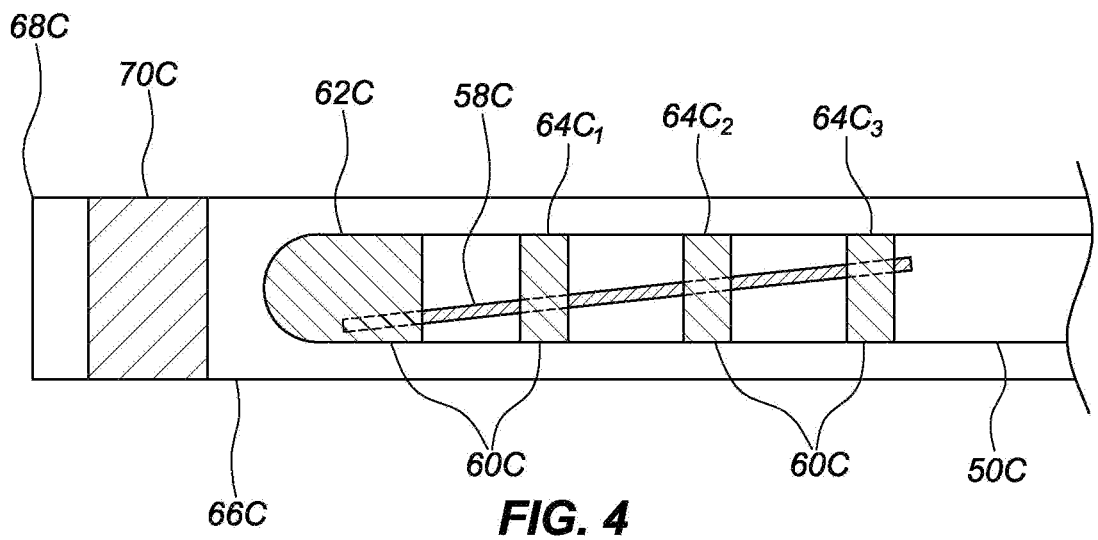
FIG. 4 is a side view of a catheter and an introducer, where the catheter includes a longitudinal sensor member, where the longitudinal member is offset from a longitudinal axis of the catheter and in a known position in relation to a plurality of electrodes positioned on a distal end portion of the catheter, in accordance with embodiments of the present disclosure.

FIG. 4 is a side view of a catheter and an introducer, where the catheter includes a longitudinal sensor member, where the longitudinal member is offset from a longitudinal axis of the catheter and in a known position in relation to a plurality of electrodes positioned on a distal end portion of the catheter, in accordance with embodiments of the present disclosure. The catheter 56C can include a longitudinal sensor member 58C and a plurality of electrodes 60C.

Similar to FIGS. 2A-B, 3, the catheter 56C in FIG. 4 can be any suitable type of catheter. Also similar to FIGS. 2A-B, 3, the plurality of electrodes 60C can be any suitable type of electrodes (e.g., ring electrodes). The plurality of electrodes 60C can include any suitable number of electrodes on the catheter 56C (e.g., a tip electrode 62C and three ring electrodes $64C_{1-3}$).

The longitudinal sensor member 58C of FIG. 4 can be made from a material that facilitates detection by a sensor (e.g., a magnetic sensor, a material with a high magnetic permeability such as Mu metal, Metglas, etc.). In some embodiments, the longitudinal sensor member 58C can be a different size and/or shape (e.g., a circle, an oval, a square, etc.) including variations in the shape along the longitudinal sensor member 58C (e.g., wider/narrower at the ends, wider/narrower at other areas between the ends, formed into a repeating "S" shape, etc.). The longitudinal sensor member 58C can be placed so the location of the member is known in relation to the position of one or more of the plurality of electrodes 60C. For example the middle or center of each corresponding sensor member of the longitudinal sensor member 58C can be aligned with the middle or center of the plurality of electrodes 60C. In other embodiments, the longitudinal sensor member can extend under all or a portion of each or some of the plurality of electrodes 60C (e.g., under a portion of all four exemplary electrodes in FIG. 4 or under a portion of two or three of the electrodes in the four exemplary electrodes in FIG. 4).

The longitudinal member 58C can be offset from the longitudinal axis of the catheter (e.g., not aligned). For example, the longitudinal member can be angled where the longitudinal axis of the longitudinal member 58C forms an angle $\theta$ with the longitudinal axis of the catheter 56C. The angle $\theta$ can be any suitable angle greater than 0°.

The catheter 56C can be used with an elongate medical device such as the introducer 66C, where the introducer 66C can be used to assist with deploying and locating the catheter 56C to a location in a body (e.g., heart tissue). The introducer 66C can have a distal end 68C. The introducer 66C can include a sensor 70C (e.g., a coil) proximate the distal end 68C. The sensor 70C can be configured to detect, for example, a proximity of the plurality of longitudinal sensor members. The sensor 70C can generate a signal where the signal provides information about the proximity of the plurality of longitudinal sensor members 58C to the sensor 70C (discussed in greater detail below). The information about the proximity of the longitudinal sensor member 58C to the sensor 70C can be used by a position detection module that is part of the ECU to determine a position of the distal end 68C of the catheter 56C in relation to the distal end 68C of the introducer 66C because of the known distances/relationship between the longitudinal sensor member 58C and the plurality of electrodes 60C.

As described herein, the position detection module can include, for example, a processor and a memory storing non-transitory computer-readable instructions, as discussed herein (e.g., as part of the ECU 42, or a separate processor and a separate memory, or a combination of the two). The ECU 42 may be programmed with a computer program (e.g., software) encoded on a computer-readable storage medium for assessing for assessing the distances between a plurality of sensor members and one or more sensors. The instructions can be executable to compute, for example, distances between the longitudinal sensor member 58C and/or a distal end (e.g., the tip electrode 62C) of the catheter 56C and the distal end 68C of the introducer 66C, the rate of change in the distances, or other characteristics related to the position of the distal end of the catheter 56C in relation to the distal end 68C of the introducer 66C. The program can include code for calculating a value responsive to magnitudes of, for example, a voltage between the longitudinal sensor member 58C and the sensor 70C.

Figure 5:
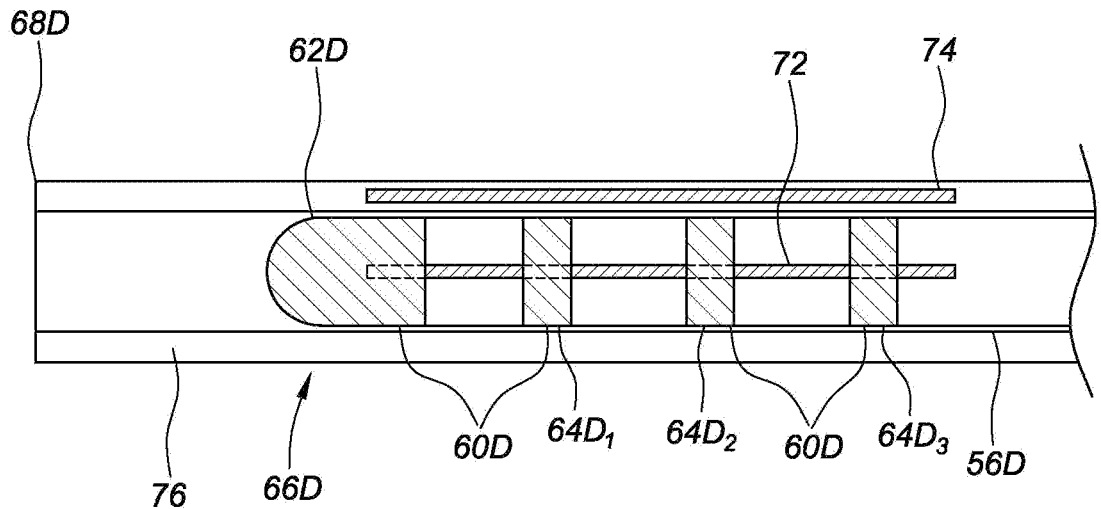
FIG. 5 is a side view of a catheter and an introducer, where the catheter includes a first longitudinal sensor member, where the first longitudinal member is aligned with a longitudinal axis of the catheter and in a known position in relation to a plurality of electrodes positioned on a distal end portion of the catheter, in accordance with embodiments of the present disclosure.

FIG. 5 is a side view of a catheter and an introducer, where the catheter includes a first longitudinal sensor member, where the first longitudinal member is aligned with a longitudinal axis of the catheter and in a known position in relation to a plurality of electrodes positioned on a distal end portion of the catheter, in accordance with embodiments of the present disclosure. The catheter 56D can include a first longitudinal sensor member 72 and a plurality of electrodes 58D. The introducer 66D can include a second longitudinal member 74.

Similar to FIGS. 2A-4, the catheter 56D in FIG. 5 can be any suitable type of catheter. Also similar to FIGS. 2A-4, the plurality of electrodes 60D can be any suitable type of electrodes (e.g., ring electrodes). The plurality of electrodes 60D can include any suitable number of electrodes on the catheter 56D (e.g., a tip electrode 62D and three ring electrodes $64D_{1-3}$).

The first and second longitudinal sensor members 72, 74 of FIG. 5 can be made from a material that facilitates detection by a sensor (e.g., a magnetic sensor, a material with a high magnetic permeability such as Mu metal, Metglas, etc.). In some embodiments, the first and/or the second longitudinal sensor members 72, 74 can be a different size and/or shape (e.g., a circle, an oval, a square, etc.) including variations in the shape along the first and/or the second longitudinal sensor members 72, 74 (e.g., wider/narrower at the ends, wider/narrower at other areas between the ends, formed into a repeating "S" shape, etc.).

The first longitudinal sensor member 72 can be placed so the location of the member is known in relation to the position of a corresponding electrode from the plurality of electrodes 60D. This can occur, for example, when the distal ends of both the catheter and the introducer are aligned (e.g., catheter 56D and introducer 66D). For example the first longitudinal sensor member 74 can be aligned with the middle or center of the plurality of electrodes 60D. In other embodiments, the first longitudinal sensor member 72 can extend under all or a portion of each or some of the plurality of electrodes 60D (e.g., under a portion of all four exemplary electrodes in FIG. 4 or under a portion of two or three of the electrodes in the four exemplary electrodes in FIG. 4).

The second longitudinal sensor member 74 can be coupled with the introducer 66D. In some embodiments, the second longitudinal sensor member 74 can be embedded in a wall 76 of the introducer 66D. In other embodiments, the second longitudinal sensor member 74 can be coupled with an interior wall or an exterior wall of the introducer 66D (not shown).

The catheter 56D can be used with an elongate medical device such as the introducer 66D, where the introducer 66D can be used to assist with deploying and locating the catheter 56D to a location in a body (e.g., heart tissue). The introducer 66D can have a distal end 68D. The second longitudinal sensor member 74 can be configured to detect, for example, a proximity of the first longitudinal sensor member 72. The second longitudinal sensor member 74 can generate a signal where the signal provides information about the proximity of the first longitudinal sensor member 72 to the second longitudinal sensor member 74 (discussed in greater detail below). The information about the proximity of the first longitudinal sensor member 72 to the second longitudinal sensor member 74 can be used by a position detection module that is part of the ECU to determine a position of the distal end 68D of the catheter 56D in relation to the distal end 68D of the introducer 66D because of the known distances/relationship between the first longitudinal sensor member 72 and the plurality of electrodes 60D.

As described herein, the position detection module can include, for example, a processor and a memory storing non-transitory computer-readable instructions, as discussed herein (e.g., as part of the ECU 42, or a separate processor and a separate memory, or a combination of the two). The ECU 42 may be programmed with a computer program (e.g., software) encoded on a computer-readable storage medium for assessing for assessing the distances between a plurality of sensor members and one or more sensors. The instructions can be executable to compute, for example, distances between the first longitudinal sensor member 72 and/or a distal end (e.g., the tip electrode 62D) of the catheter 56D and the distal end 68D of the introducer 66D, the rate of change in the distances, or other characteristics related to the position of the distal end of the catheter 56D in relation to the distal end 68D of the introducer 66D. The program can include code for calculating a value responsive to magnitudes of, for example, a voltage between the first longitudinal sensor member 72 and the second longitudinal sensor member 74.

Figure 6:
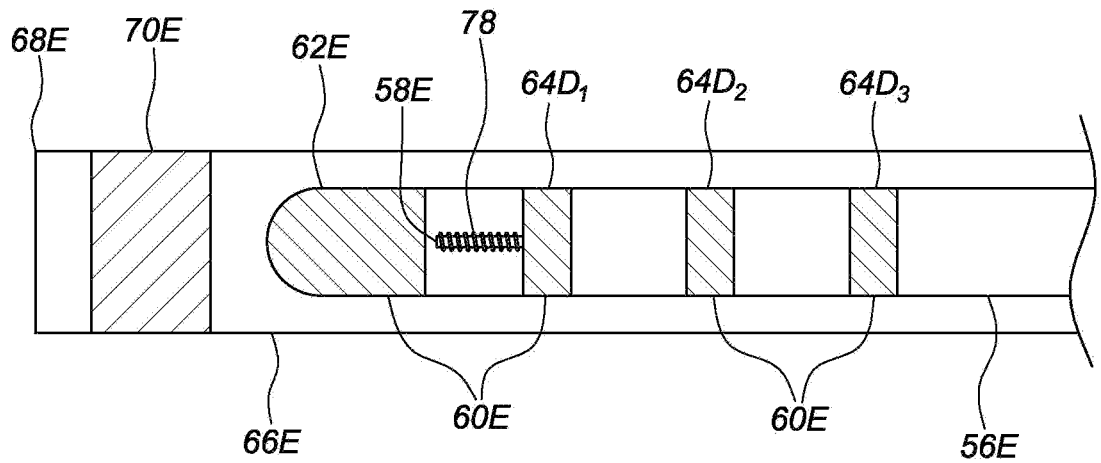
FIG. 6 is a side view of a catheter with a longitudinal sensor member and an introducer with a sensor, where the longitudinal sensor member includes a coil coupled with the longitudinal sensor member, where the longitudinal member is aligned with a longitudinal axis of the catheter and in a known position in relation to the plurality of electrodes positioned on a distal end portion of the catheter, in accordance with embodiments of the present disclosure.

FIG. 6 is a side view of a catheter with a longitudinal sensor member and an introducer with a sensor, where the longitudinal sensor member includes a coil coupled with the longitudinal sensor member, where the longitudinal member is aligned with a longitudinal axis of the catheter and in a known position in relation to the plurality of electrodes positioned on a distal end portion of the catheter, in accordance with embodiments of the present disclosure. The catheter 56E can include a longitudinal sensor member 58E with a coil 78 and the introducer 66E can include a sensor 70E.

Similar to FIGS. 2A-5, the catheter 56E in FIG. 6 can be any suitable type of catheter. Also similar to FIGS. 2A-5, the plurality of electrodes 60E can be any suitable type of electrodes (e.g., ring electrodes). The plurality of electrodes 60E can include any suitable number of electrodes on the catheter 56E (e.g., a tip electrode 62E and three ring electrodes $64E_{1-3}$).

The longitudinal sensor member 58E can be similar to the embodiment shown in FIG. 2A (e.g., made from a material that facilitates detection by a sensor (e.g., a magnetic sensor, a material with a high magnetic permeability such as Mu metal, Metglas, etc.). The coil 78 can be coupled with the sensor member 58E and can be made of any suitable material (e.g., a conductive wire, etc.). The coil 78 can be any suitable size material (e.g., a single diameter of wire, etc.). The coil 78 can be any suitable configuration (e.g., where the coil 78 and can be coupled with half of the longitudinal sensor member 58E, coupled with three-quarters of the longitudinal sensor member 58E, etc.) on the longitudinal sensor member 58E. In some embodiments, the longitudinal sensor member 58E can include a plurality of coils (not shown). Spacing of the plurality of coils can be equal or varied. The coil can, for example, include equal or unequal spaced windings, or coils wound at an angle with respect to the sensor member 58E. In some embodiments (not shown), multiple longitudinal sensor members 58E with corresponding coils 78 could be, for example, spaced along a length of a catheter (e.g., catheter 56E), or around a circumference, and the multiple longitudinal sensor members 58E and coils 78 may be, for example, of unequal lengths and unequal spacing. In still another embodiments (not shown), a single longitudinal sensor member 58E can be used with multiple coils 78 spaced along the single longitudinal sensor member.

In some embodiments (not shown), the longitudinal sensor member 58E with the coil 78 can be a different size and/or shape (e.g., a circle, an oval, a square, etc.). The longitudinal sensor member 58E with the coil 78 can be placed so the location of the longitudinal sensor member 58E is known in relation to the position of a corresponding electrode from the plurality of electrodes 60E. For example, the middle or center of the longitudinal sensor member 58E with a coil 78 can be aligned with the middle or center of a corresponding electrode from the plurality of electrodes 60E.

The catheter 56E can be used with an elongate medical device such as an introducer 66E, where the introducer 66E can be used to assist with deploying and locating the catheter 56E to a location in a body (e.g., heart tissue). The introducer 66E can have a distal end 68E. The introducer 66E can include a sensor 70E (e.g., a coil) proximate to the distal end 68E. The sensor 70E can be configured to detect, for example, a proximity of the plurality of longitudinal sensor members 58E. The sensor 70E can generate a signal where the signal provides information about the proximity of the plurality of longitudinal sensor members 58E to the sensor 70E (discussed in greater detail below). The known distances between the plurality of electrodes 60E and the longitudinal sensor member 58E can be used to determine the position of the catheter 56E with respect to the introducer 66E (e.g., an amount of the catheter 56E that extends beyond the distal end 68E of the introducer 66E). The information about the proximity of the longitudinal sensor member 58E with the coil 78 to the sensor 70E can be used by a position detection module that is part of the ECU to determine a position of the distal end 68E of the catheter 56E in relation to the distal end 68E of the introducer 66E because of the known distances/relationship between the longitudinal sensor member 58E and the plurality of electrodes 60E.

Figure 7A:
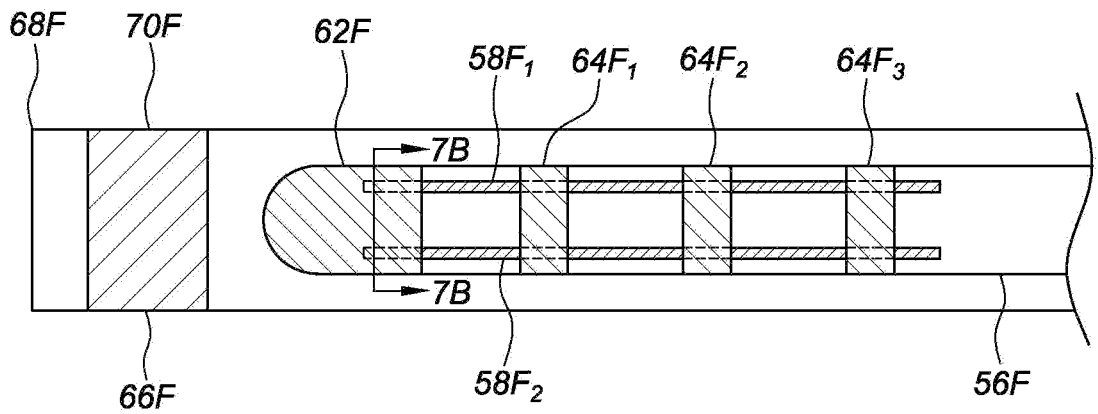
FIG. 7A is a schematic view of a catheter with a first longitudinal sensor member and a second longitudinal sensor member of a plurality of longitudinal sensor members, where each of the plurality of longitudinal sensor members can be aligned with a longitudinal axis of the catheter and spaced radially around the catheter, in accordance with embodiments of the present disclosure.

FIG. 7A is a schematic view of a catheter with a first longitudinal sensor member and a second longitudinal sensor member of a plurality of longitudinal sensor members, where each of the plurality of longitudinal sensor members can be aligned with a longitudinal axis of the catheter and spaced radially around the catheter, in accordance with embodiments of the present disclosure.

Figure 7B:
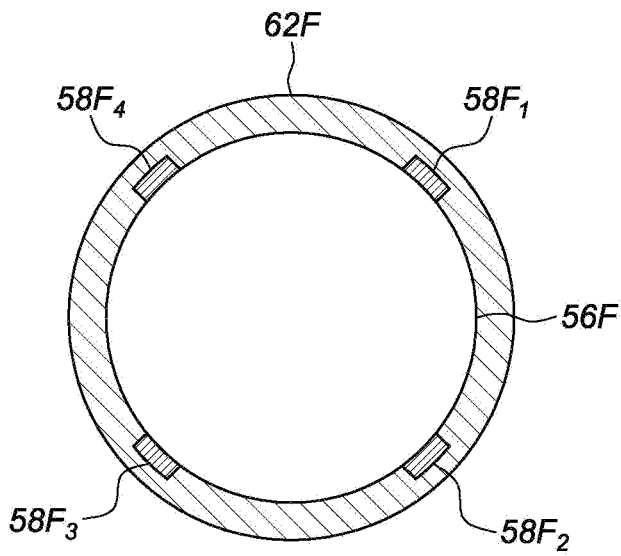
FIG. 7B is a cross-sectional view of the catheter of FIG. 7A, in accordance with embodiments of the present disclosure.

In some embodiments, the longitudinal sensor members $58F_{1-4}$ can be arranged as shown in FIGS. 7A and 7B where each of the four longitudinal sensor members $58F_{1-4}$ can be equally placed around the circumference of the catheter 56F. Two longitudinal sensor members are visible in FIG. 7A, ($58F_1$ and $58F_2$) as the other two ($58F_3$ and $58F_4$) are hidden in that view (see FIG. 7B).

In some embodiments, the number of the longitudinal sensor members 58F can be varied (e.g., two, three, five, etc.) and the spacing between the longitudinal sensor members can also vary. The shape of the longitudinal sensor members can also vary. FIG. 7A shows a rectangular shape for the longitudinal sensor members $58F_{1-4}$. However, in some embodiments the longitudinal sensor members can be oval, square, triangular, etc. The longitudinal length of the longitudinal sensor members can vary.

In some embodiments the orientation of the longitudinal sensor members can be varied. For example, one or more members could be arranged in a helical pattern along a distal end of a catheter (not shown). A combination of patterns could be combined with multiple longitudinal sensor members (e.g., two longitudinal sensor members in helical patterns and two longitudinal sensor members in linear arrangement aligned with longitudinal axis of catheter, etc.).

FIG. 7B is a cross-sectional view of the catheter of FIG. 7A, in accordance with embodiments of the present disclosure. The catheter 56F can include an electrode, for example, the tip electrode 62F (one of the plurality of electrodes 60F shown in FIG. 7A) and a plurality of longitudinal sensor members 58F. In one embodiment, as shown in FIG. 7B (a cross-section of catheter 56F along the line 7B-7B of FIG. 7A) there can be four longitudinal sensor members $58F_{1-4}$. Radial spacing between the longitudinal sensor members $58F_{1-4}$ can be equal as shown in FIG. 7B (e.g., $58F_1$ at 45°, $58F_2$ at 135°, $58F_3$ at 225°, and $58F_4$ at 315°) or the radial spacing can be varied (not shown) in other embodiments. Multiple longitudinal sensor members can allow for evaluation of a "roll" (e.g., a rotational position determination) of the catheter 56F.

Figure 8:
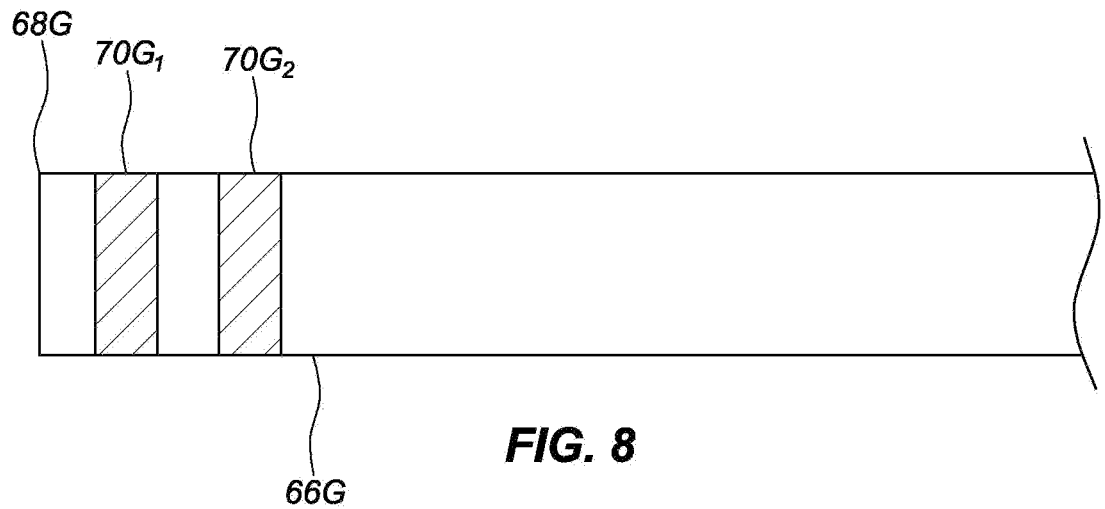
FIG. 8 is a side view of an introducer with a first sensor and a second sensor proximate a distal end of the introducer, in accordance with embodiments of the present disclosure.

FIG. 8 is a side view of an introducer with a first sensor and a second sensor proximate a distal end of the introducer, in accordance with embodiments of the present disclosure. The introducer 66G can include a first sensor $70G_1$ and a second sensor $70G_2$ proximate a distal end 68G of the introducer 66G. The introducer 66G can be used with any of the exemplary catheters described herein, including those described in FIGS. 2A-7B.

The first sensor $70G_1$ can be similar to the sensor described in FIGS. 2A-7B above to detect a signal from a sensor member. The second sensor $70G_2$ can be used for determining a position of the introducer using a positioning system (e.g., a magnetic coil sensor). The first sensor $70G_1$ and second sensor $70G_2$ may be the same or different (e.g., more or less windings of wire, a different core material, longer/shorter) in order to create differing nominal output of signals and/or other properties.

Figure 9A:
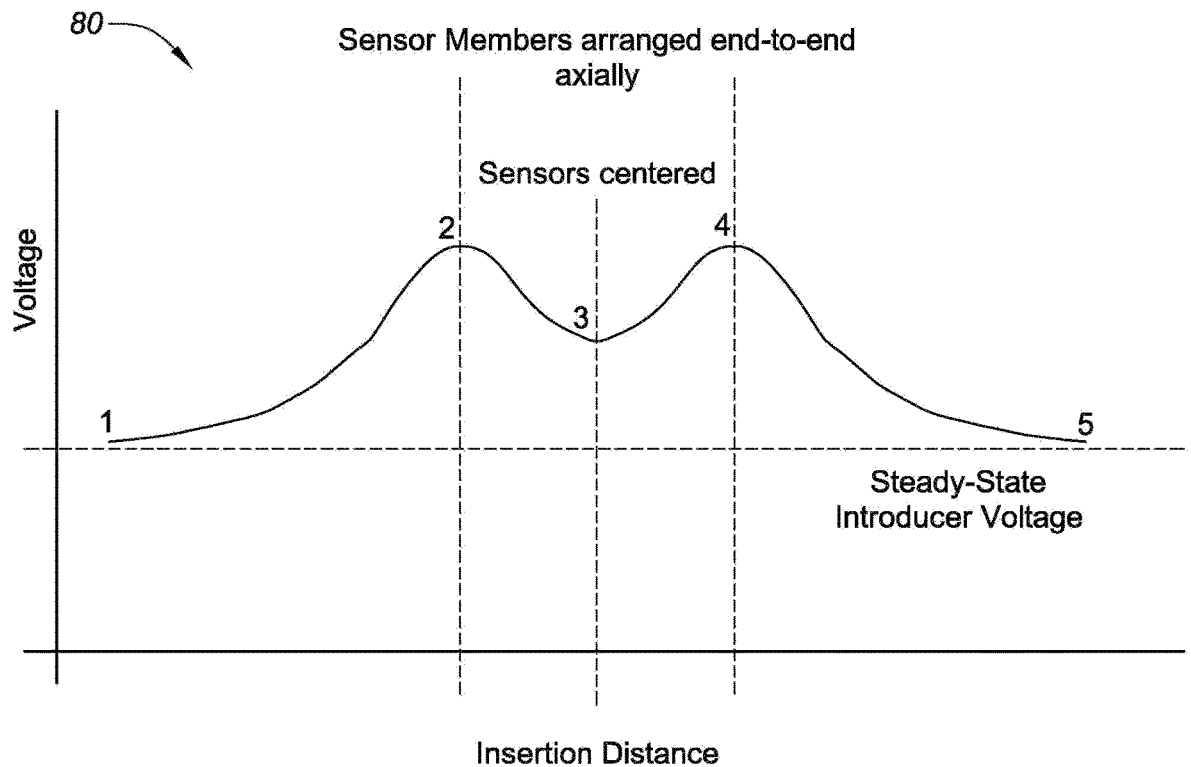
FIG. 9A show an exemplary relationship between a voltage output of a sensor on an introducer compared to the insertion distance of a sensor member of a high magnetic permeability material as the distance between the sensor and the sensor member varies, in accordance with embodiments of the present disclosure.

FIG. 9A show an exemplary relationship between a voltage output of a sensor on an introducer compared to the insertion distance of a sensor member of a high magnetic permeability material as the distance between the sensor and the sensor member varies, in accordance with embodiments of the present disclosure.

The exemplary embodiment of FIG. 9A represents two sensor members of a high magnetic permeability material that are longer than they are wide (e.g., a rectangular strip) where the long sides are aligned with a longitudinal axis of the introducer and the inner sheath. A first sensor member is coupled with the introducer. A second sensor member can be coupled with the inner sheath (e.g., a catheter). As the inner sheath (e.g., catheter 56E) is moved (longitudinally and/or rotationally) the distance between the first sensor member and the second sensor member changes. As the distance changes, a difference in voltage measured at the first sensor member can be represented by the graph 80 in FIG. 9A. When the two sensor members (e.g., are centered (e.g., both centers and the ends all line up) the voltage can drop to a point 3 on the graph 80. As the catheter (e.g., catheter 56E) is moved with respect to the introducer (e.g., introducer 66E) the distance between the centers of the sensor members increases and the voltage can increase as shown in FIG. 9A. The voltage can decrease (e.g., moving from point 2 to 1 and points 4 to 5) as shown in FIG. 9A when the catheter is further moved apart with respect to the introducer.

Changes in voltage can be a characteristic of the relationship of changes in distance between the first and the second sensor members. Other characteristics that can be used include, for example, measuring changes in any one or more of a current, a magnetic field strength, a magnetic flux density, and/or other properties related to sensors and/or high magnetic permeability material.

Figure 9B:
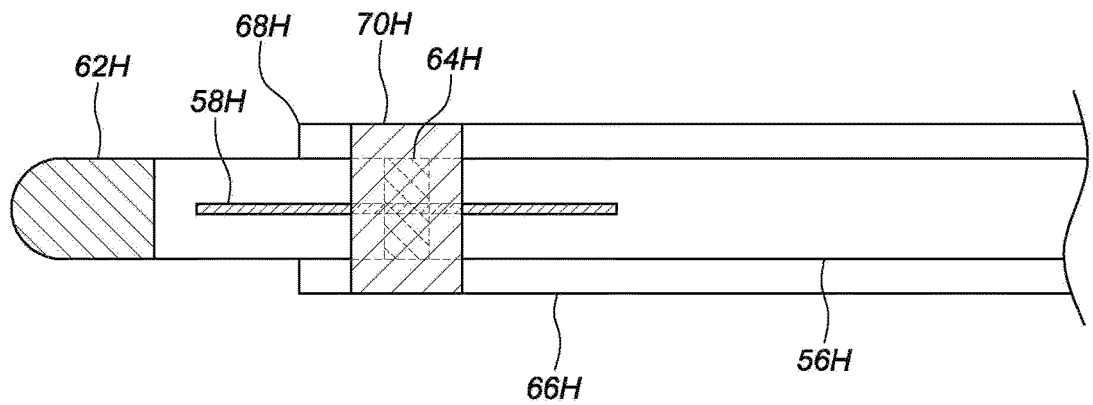
FIG. 9B shows an exemplary embodiment of FIG. 6 where the longitudinal sensor member has moved toward the distal end of the introducer, and is centered on the sensor, in accordance with embodiments of the present disclosure.

FIG. 9B shows an exemplary embodiment similar to FIG. 3, where a longitudinal sensor member is centered on a sensor, in accordance with embodiments of the present disclosure. In this embodiment, the longitudinal sensor member 58H is centered on the ring electrode 64H and centered under a sensor 70H and the longitudinal sensor member 58H is proximate the distal end 68H of the catheter 56H. Compared to FIG. 3, FIG. 9B shows a catheter 56H moved within an introducer 66H, which also moved a longitudinal sensor member 58H and a ring electrode 64H.

When the longitudinal sensor member 58H is centered under the sensor 70H, the peak voltage 3 in FIG. 9A can correspond to the configuration shown in FIG. 9B. Variations of the arrangement in FIG. 9B can correspond to other portions of the graph 80 in FIG. 9A (e.g., peak voltage 2 can correspond to the longitudinal sensor member 58H being proximate the sensor 70H but further from the distal end 68H of the catheter 56H, and peak voltage 4 can correspond to the longitudinal sensor member 58H being proximate the sensor 70H but closer to the distal end 68H).

With further reference to FIG. 1, embodiments of the present disclosure can include a system 10 for generating information about distances between, for example, a sensor, a sensor member, and locations of the sensor. The ECU 42 can be used to analyze and interpret the signals generated as the catheter moves within the introducer. In some embodiments, the ECU 42 can include a processor and memory storing non-transitory computer-readable instructions, as discussed herein. The instructions can be executable to compute distances between, for example, a sensor and a sensor member to determine a location of the sensor member (which can be changing over time).

As described herein, some embodiments can include a position detection module (e.g., as part of ECU 42 in FIG. 1). The position detection module can be configured to analyze a relative position of a catheter (e.g., catheter 56A and its corresponding introducer (e.g., introducer 66A). The ECU (e.g., ECU 42) can include a memory that is configured to keep track of the relative positions of the catheter and the corresponding sensor members (e.g., longitudinal sensor members $58A_{1-4}$) and/or the current exit or entrance state of the catheter with respect to the introducer. For example, the system (e.g., system 10) can keep track of which electrodes and/or sensor members are located inside and/or outside of the introducer and can also provide this information to an operator via, for example, a graphical user interface (GUI) and/or a display (e.g., display 40).

The signals generated as the catheter moves within the introducer can include, for example, a voltage, a magnetic field strength, an inductance, a resistance, a current, or other type of signal typically generated by a sensor that can be used to detect movement and/or proximity of a sensor member described herein (e.g., a longitudinal sensor member made of a high magnetic permeability material).

The instructions can be executed to determine proximity of a sensor member to, for example, a sensor, another sensor member, or other device, based on changes in signals (e.g., changes in voltage, current, magnetic field, etc.). For example, with reference to FIG. 6, as the catheter 56E moves within the introducer 66E, the longitudinal sensor member 58E, the ECU 42 can monitor a signal from the longitudinal sensor member 58E and/or the coil 78 and determine, based on the signal, a position of the longitudinal sensor 58E with respect to the introducer 66E. When the distances and/or positions of the electrodes (e.g., the tip electrode 62E and the ring electrodes $64E_{1-3}$) on the catheter 56E are known with respect to the position and/or location of the longitudinal sensor member 58E and/or the coil 78 data regarding the relative position of the catheter 56E can be output (e.g., visual images and/or information) to a display (e.g., the display 40 of FIG. 1) or to a handle (e.g., the handle 24) through lights, sounds, vibration, or other feedback.

Figure 10A:
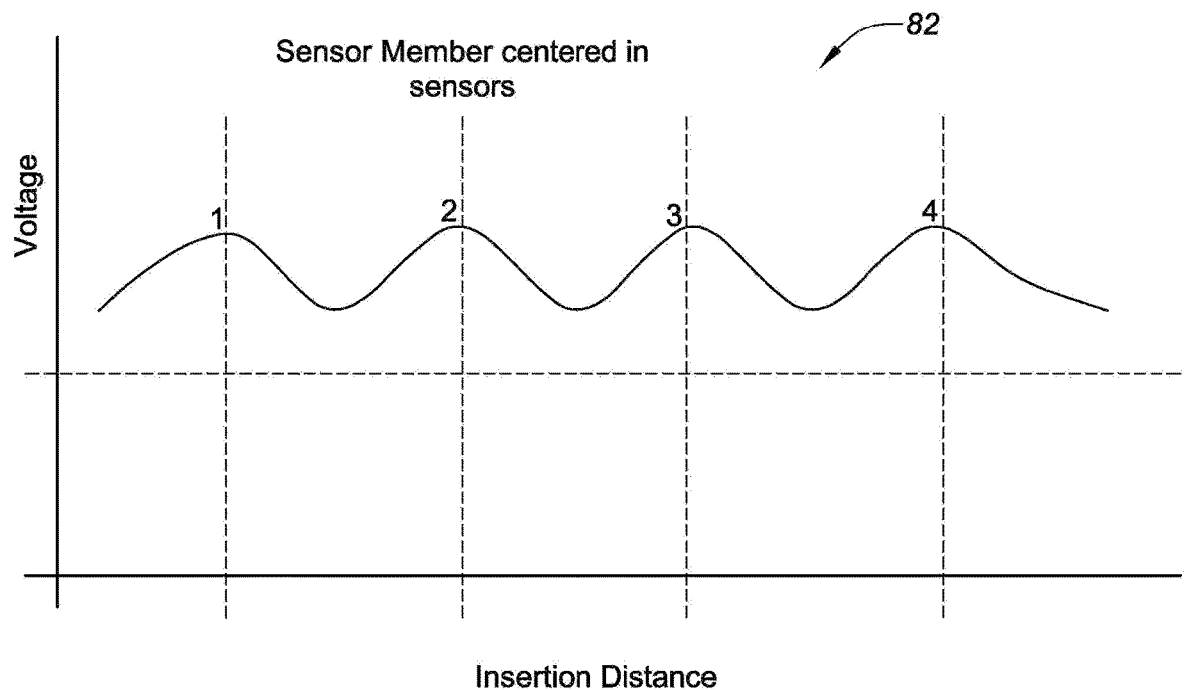
FIG. 10A shows an exemplary relationship between a voltage output of a sensor on an introducer compared to the insertion distance of four sensor members of a high magnetic permeability material of equal size as the distance between the sensor and the sensor members varies, in accordance with embodiments of the present disclosure.

FIG. 10A shows a graph of an exemplary relationship between a voltage output of a sensor on an introducer compared to the insertion distance of four sensor members of a high magnetic permeability material of equal size as the distance between the sensor and the sensor members varies, in accordance with embodiments of the present disclosure. As described herein, changing a distance between sensor members and a sensor can vary a voltage output measured at the sensor. For example, with reference to FIGS. 2A and 10A, as the catheter 56 is moved (which also moves the plurality of longitudinal sensor members $58_{1-4}$ coupled with the catheter 56) with respect to the introducer 66, a voltage can be measured across the sensor 70. The voltage can change as each of the plurality of longitudinal sensor members $58_{1-4}$ moves closer to (and further from) the sensor 70.

A magnitude of the voltage on the graph can indicate a proximity of each of the plurality of sensor members to a sensor. For example, a larger sensor member can generate a larger voltage magnitude and a smaller sensor member can generate a smaller voltage magnitude on the graph. A shape of the graph (e.g., the width of each peak or "blip", the curvature of the line, etc.) can indicate, for example, the shape, size, and/or type of the plurality of sensor members in a particular embodiment. For example, a larger sensor member can generate a wider peak section with a flatter profile near a peak voltage and a smaller sensor member can generate a narrower peak section with a steeper profile near the peak voltage on the graph.

The exemplary embodiment of FIG. 10A represents a first longitudinal sensor member $58_1$ that is longer than it is wide (e.g., a rectangular strip) where the long sides are aligned with a longitudinal axis of the introducer and the inner sheath. The first longitudinal sensor member $58_1$ can be coupled with the introducer. The plurality of sensor members $58_{1-4}$ can be coupled with the inner sheath (e.g., a catheter, or other device). Each of the plurality of sensor members $58_{1-4}$ can have the same dimensions. In some embodiments, each of the sensor members can be a sensor member that is wrapped around the catheter to form, for example, a ring sensor (e.g., a planar sensor member that is wrapped around the catheter).

As the inner sheath (e.g., catheter 56) is moved (longitudinally and/or rotationally), the distance between the sensor 70 and each of the sensor members changes. As the distance between the sensor 70 and each of the plurality of longitudinal sensor members $58_{1-4}$ changes, a difference in voltage measured at the sensor 70 can be represented by a graph 82 in FIG. 10A. Each of the peak voltages shown in FIG. 10A can correspond to a position of one of the plurality of sensor members $58_{1-4}$ (e.g., this embodiment includes four sensor members). For example, in FIG. 10A, a peak voltage 1 can correspond to a position of the longitudinal sensor member $58_1$ proximate to the tip electrode 62 being centered on the sensor 70. A peak voltage 2 can correspond to the position of the longitudinal sensor member $58_2$ proximate the ring electrode $64_1$ being centered on the sensor 70, a peak voltage 3 can correspond to a position of the longitudinal sensor member 58 (proximate the ring electrode $64_3$) being centered on the sensor 70 the position of the longitudinal sensor member 58 (proximate the ring electrode $64_3$) being centered on the sensor 70 can correspond to a peak voltage 3, and the position of the longitudinal sensor member 58 (proximate the ring electrode $64_4$) being centered on the sensor 70 can correspond to a peak voltage 4. The peak voltages in FIG. 10A can be the same magnitude and shape in this embodiment because the dimensions of the plurality of longitudinal sensor members $58_{1-4}$ are the same.

Figure 10B:
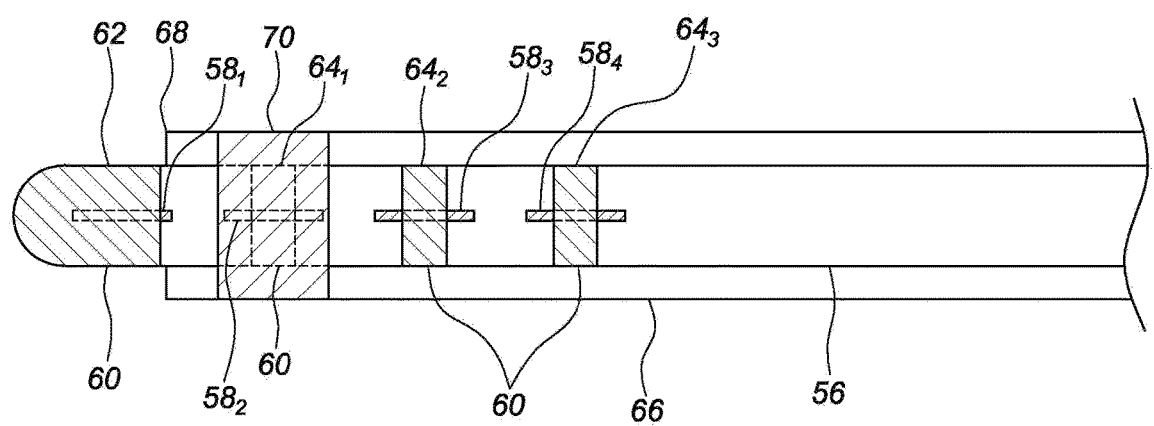
FIG. 10B shows an exemplary embodiment of FIG. 2A where one of the plurality of longitudinal sensor members has moved outside of the distal end of the introducer, past the sensor, in accordance with embodiments of the present disclosure.

FIG. 10B shows an exemplary embodiment of FIG. 2A where one of the plurality of longitudinal sensor members has moved outside of the distal end of the introducer, past the sensor, in accordance with embodiments of the present disclosure. FIG. 10B shows the catheter 56 moved within the introducer 66 compared to FIG. 2A, which also moved the plurality of longitudinal sensor members 58. In this embodiment, the longitudinal sensor member $58_2$ is centered under the sensor 70 and the longitudinal sensor member $58_1$ is outside the distal end 68 of the catheter 56. When the longitudinal sensor member $58_2$ is centered under the sensor 70. The peak voltage 2 in FIG. 10A can correspond to the configuration shown in FIG. 10B. Variations of the arrangement in FIG. 10B can correspond to other portions of the graph in FIG. 10A (e.g., peak voltage 3 can correspond to the longitudinal sensor member 583 being centered under the sensor 70, and peak voltage 4 can correspond to the longitudinal sensor member 584 being centered under the sensor 70).

With further reference to FIG. 1, embodiments of the present disclosure can include a system 10 for generating information about distances between, for example, a sensor, a sensor member, and locations of the sensor. The ECU 42 can be used to analyze and interpret the signals generated as the catheter moves within the introducer. In some embodiments, the ECU 42 can include a processor and memory storing non-transitory computer-readable instructions, as discussed herein. The instructions can be executable to compute distances between, for example, a sensor and a sensor member to determine a location of the sensor member (which can be changing over time).

The instructions can be executed to determine proximity of a sensor member to, for example, a sensor, another sensor member, or other device, based on changes in signals (e.g., changes in voltage, current, magnetic field, etc.). For example, with reference to FIG. 6, as the catheter 56E moves within the introducer 66E, the longitudinal sensor member 58E, the ECU 42 can monitor a signal from the longitudinal sensor member 58E and/or the coil 78 and determine, based on the signal, a position of the longitudinal sensor 58E with respect to the introducer 66E. When the distances and/or positions of the electrodes (e.g., the tip electrode 62E and the ring electrodes $64E_{1-3}$) on the catheter 56E are known with respect to the position and/or location of the longitudinal sensor member 58E and/or the coil 78 data regarding the relative position of the catheter 56E can be output (e.g., visual images and/or information) to a display (e.g., the display 40) or to a handle (e.g., the handle 24) through lights, sounds, vibration, or other feedback.

Figure 11A:
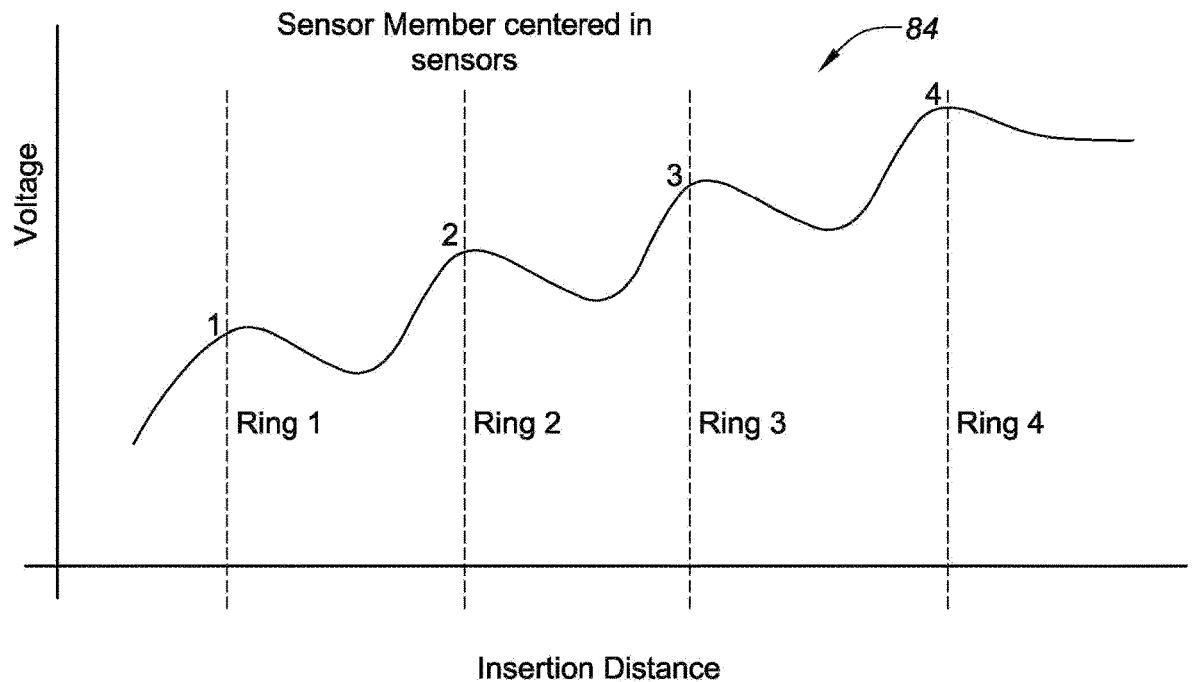
FIG. 11A shows an exemplary relationship between a voltage output of a sensor on an introducer compared to the insertion distance of four sensor members of a high magnetic permeability material of different sizes as the distance between the sensor and the high magnetic permeability members varies, in accordance with embodiments of the present disclosure.

FIG. 11A shows an exemplary relationship between a voltage output of a sensor on an introducer compared to the insertion distance of four sensor members of a high magnetic permeability material of different sizes as the distance between the sensor and the high magnetic permeability members varies, in accordance with embodiments of the present disclosure. As described herein, changing a distance between sensor members and a sensor can vary a voltage output measured at the sensor. For example, with reference to FIGS. 2B and 11A, as the catheter 56A is moved (which also moves the plurality of longitudinal sensor members 58A) with respect to the introducer 66, a voltage can be measured across the sensor 70A.

The exemplary embodiment of FIG. 11A represents a sensor member that is longer than it is wide (e.g., a rectangular strip) where the long sides are aligned with a longitudinal axis of the introducer and the inner sheath. A first high magnetic permeability member can be coupled with the introducer. A plurality of sensor members can be coupled with the inner sheath (e.g., a catheter). For example, the plurality of longitudinal sensor members $58_{1-4}$ can be arranged as shown in FIG. 2A where each of the plurality of longitudinal sensor members $58_{1-4}$ are the same size. In another embodiment, the plurality of sensor members can be, for example, a planar sensor member that is wrapped around the catheter to form, for example, a ring.

As the inner sheath (e.g., catheter 56A) is moved (longitudinally and/or rotationally) the distance between the first high magnetic permeability member (e.g., a sensor 70A) and each of the plurality of high magnetic permeability members changes. For example, in FIG. 11A, a peak voltage 1 along graph 84 can correspond to a position of the longitudinal sensor member proximate the tip electrode 62A ($58A_1$). A peak voltage 2 can correspond to the position of the longitudinal sensor member $58A_2$ proximate the ring electrode $64_1$ being centered on the sensor 70A, a peak voltage 3 can correspond to a position of the longitudinal sensor member $58A_3$ (proximate the ring electrode $64A_3$) being centered on the sensor 70A the position of the longitudinal sensor member $58A_3$ (proximate the ring electrode $64A_3$) being centered on the sensor 70A can correspond to a peak voltage 3, and the position of the longitudinal sensor member $58A_4$ (proximate the ring electrode $64_4$) being centered on the sensor 70A can correspond to a peak voltage 4. The peak voltages in FIG. 11A can be different magnitudes and shapes (e.g., compared to those in FIG. 10A and compared to each other) in this embodiment because the dimensions of the plurality of sensor members $58A_{1-4}$ are different compared to each other and compared to the plurality of sensor members $58_{1-4}$ in FIG. 10A.

As the distance changes, a difference in voltage measured at the first high magnetic permeability member can be represented by the graph 84 in FIG. 11A. Each of the peak voltages shown in FIG. 11A can correspond to one of the plurality of high magnetic permeability members (e.g., this embodiment includes four high magnetic permeability strips). The embodiment of FIG. 11A can be similar, for example, to a linear variable differential transformer (LVDT). An LVDT is an example of an electromechanical transducer that can convert rectilinear motion into an electrical signal that corresponds to the motion.

Figure 11B:
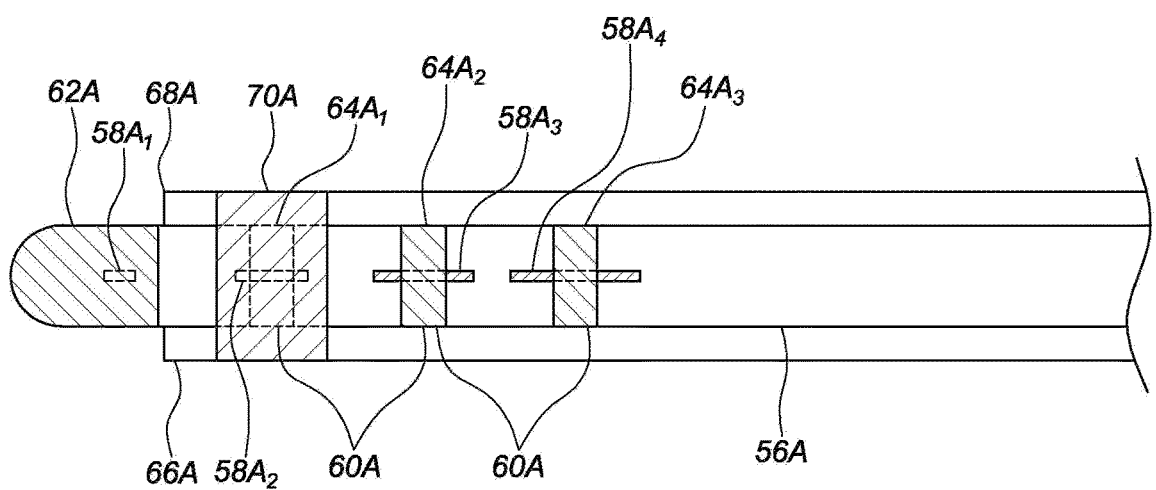
FIG. 11B shows an exemplary embodiment of FIG. 2B where one of the plurality of longitudinal sensor members has moved outside of the distal end of the introducer, past the sensor, in accordance with embodiments of the present disclosure.

FIG. 11B shows an exemplary embodiment of FIG. 2B where one of the plurality of longitudinal sensor members has moved outside of the distal end of the introducer, past the sensor, in accordance with embodiments of the present disclosure. Compared to FIG. 2B, FIG. 11B shows the catheter 56A moved within the introducer 66A, which also moved the plurality of longitudinal sensor members $58A_{1-4}$. In this embodiment, the longitudinal sensor member $58A_2$ is centered under the sensor 70A and the longitudinal sensor member $58A_1$ is outside the distal end 68A of the catheter 56A. When the longitudinal sensor member $58A_2$ is centered under the sensor 70A. The peak voltage 2 in FIG. 11A can correspond, for example, to the configuration shown in FIG. 11B. Variations of the arrangement in FIG. 11B can correspond to other portions of the graph in FIG. 11A (e.g., peak voltage 3 can correspond to a position of the longitudinal sensor member $58A_3$ being centered under the sensor 70A, and peak voltage 4 can correspond to the position of the longitudinal sensor member 584 being centered under the sensor 70A).

Figure 12A:
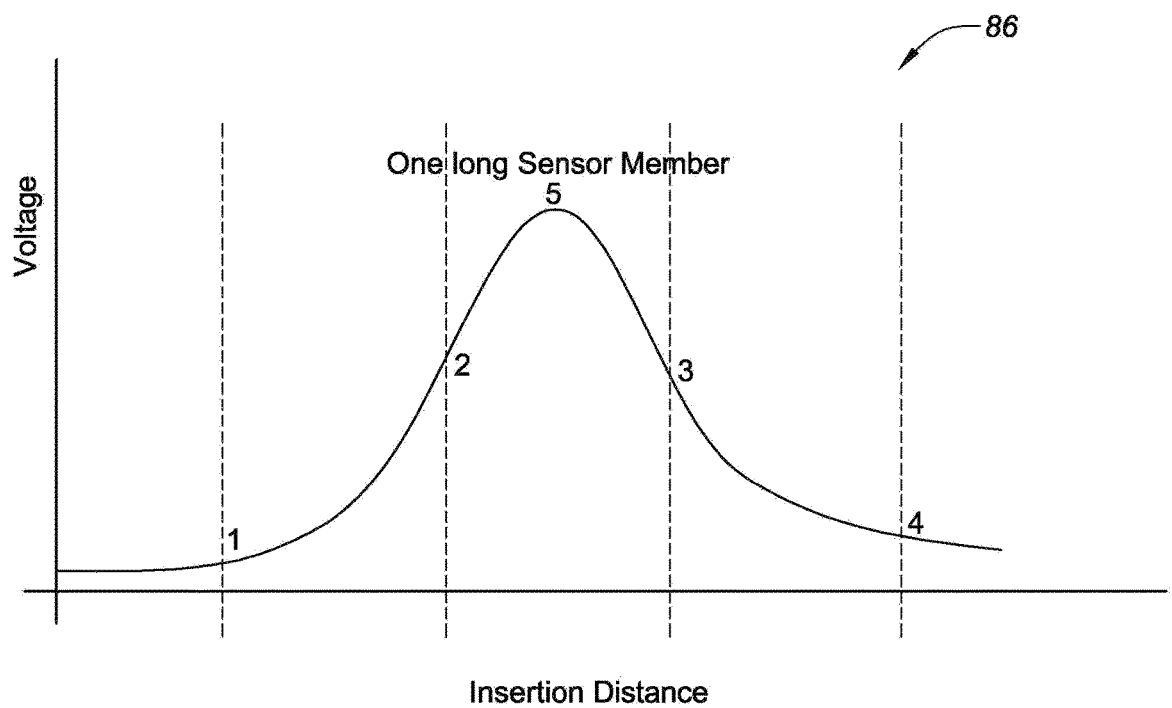
FIG. 12A shows an exemplary relationship between a voltage of a sensor on an introducer compared to the insertion distance of a sensor member of a high magnetic permeability material coupled with an inner sheath (e.g., a catheter), aligned with a longitudinal axis of the introducer and the inner guide sheath, as the distance between the sensor and the sensor member varies, in accordance with embodiments of the present disclosure.

FIG. 12A shows an exemplary relationship between a voltage of a sensor on an introducer compared to the insertion distance of a sensor member of a high magnetic permeability material coupled with an inner sheath (e.g., a catheter), aligned with a longitudinal axis of the introducer and the inner guide sheath, as the distance between the sensor and the sensor member varies, in accordance with embodiments of the present disclosure. As described herein, changing a distance between a sensor member and a sensor can vary a voltage output measured at the sensor. For example, with reference to FIGS. 3 and 12A, as the catheter 56B is moved (which also moves the longitudinal sensor member 58B coupled with the catheter 56B) with respect to the introducer 66B, a voltage can be measured across the sensor 70B.

FIG. 12A shows an exemplary embodiment of FIG. 3 where the sensor 70B is coupled with the introducer 66B and the longitudinal sensor member 58B is coupled with the catheter 56B. The longitudinal sensor member 58B can be a single sensor member that is longer than it is wide (e.g., a rectangular strip) where the long sides are aligned with a longitudinal axis of the catheter 56B. The sensor 70B can be coupled with an introducer. As described above, the plurality of electrodes 60B can be any suitable type of electrodes (e.g., ring electrodes). The plurality of electrodes 60B can include any suitable number of electrodes on the catheter 56B (e.g., a tip electrode 62B and three ring electrodes $64B_{1-3}$).

As the inner sheath (e.g., catheter 56B) is moved (longitudinally and/or rotationally) the distance between the longitudinal sensor member 58B and each of the plurality of electrodes 60B changes. As the distance changes, a difference in voltage measured at the sensor 70B can be represented by graph 86 in FIG. 12A. In some embodiments, the plurality of electrodes 60B can be equally spaced from each other. When the midpoint of the longitudinal sensor member 58B is centered with the sensor 70B, the voltage measured at the sensor can be a maximum as shown in FIG. 12A. As the longitudinal sensor member 58B moves from that center point (e.g., to the left or to the right) the voltage can decrease.

Figure 12B:
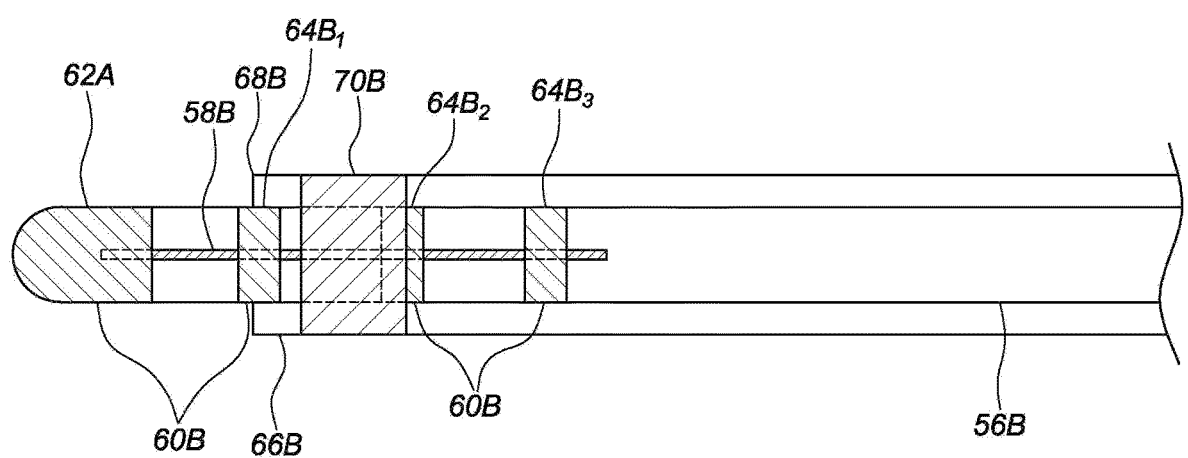
FIG. 12B shows an exemplary embodiment of FIG. 3 where a portion of the longitudinal sensor member has moved outside of the distal end of the introducer, past the sensor, in accordance with embodiments of the present disclosure.

FIG. 12B shows an exemplary embodiment of FIG. 3 where a portion of the longitudinal sensor member has moved outside of the distal end of the introducer, past the sensor, in accordance with embodiments of the present disclosure. Compared to FIG. 3, FIG. 12B shows the catheter 56B moved within the introducer 66B, which also moved the longitudinal sensor member 58B. In this embodiment, the longitudinal sensor member 58B can be centered under the sensor 70B and a portion of the longitudinal sensor member 58B can be outside the distal end 68B of the catheter 56B. When the longitudinal sensor member 58B is centered under the sensor 70B, the peak voltage 5 in FIG. 12A can correspond to the configuration shown in FIG. 12B. Variations of the arrangement in FIG. 12B can correspond to other portions of the graph in FIG. 12A. For example, voltage 2 can correspond to a position of the longitudinal sensor member 58B being positioned with ring electrode $64B_1$ centered under the sensor 70A, voltage 3 can correspond to the position of the longitudinal sensor member 58B being positioned with ring electrode $64B_2$ centered under the sensor 70A, voltage 4 can correspond to a position of the longitudinal sensor member 58B being positioned with ring electrode $64B_3$ centered under the sensor 70A, and voltage 1 can correspond to a position of the longitudinal sensor member 58B being positioned with the tip electrode 62A centered under the sensor 70A.

A display (e.g., the display 40 of FIG. 1) can display information represented by any of the embodiments described herein. For example, the information can include values for an amount of a catheter that is currently outside of an introducer, whether the catheter is moving into or out of the introducer (e.g., change in distance of catheter outside the introducer or inside the introducer), the values used to calculate the amount (e.g., voltage, magnetic field strength, etc.), and/or a graphical representation of any of the information. The information can be processed and/or determined by an ECU (e.g., ECU 42), including, in some embodiments, part of the functionality of a position detection module.

Although at least one embodiment of an apparatus for detecting catheters to introducers has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements and can also include elements that are part of a mixture or similar configuration. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

It should be understood that the system 10, particularly ECU 42, as described above may include conventional processing apparatus known in the art, capable of executing pre-programmed instructions stored in an associated memory, all performing in accordance with the functionality described herein. It is contemplated that the methods described herein, including without limitation the method steps of embodiments of the disclosure, will be programmed in a preferred embodiment, with the resulting software being stored in an associated memory and where so described, may also constitute the means for performing such methods. Implementation of the embodiments, in software, in view of the foregoing enabling description, would require no more than routine application of programming skills by one of ordinary skill in the art. Such a system may further be of the type having both ROM, RAM, a combination of non-volatile and volatile (modifiable) memory so that the software can be stored and yet allow storage and processing of dynamically produced data and/or signals.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An apparatus for detecting a relative position of medical devices located within a human body, the apparatus comprising:
    an outer elongate member;
    an inner elongate member comprising
        a plurality of electrodes,
    a first sensor member having a first length,
    wherein the inner elongate member is configured to move within the outer elongate member, wherein the first sensor member is configured to generate a first signal indicative of movement of the inner elongate member relative to the outer elongate member and wherein the first sensor member extends under a portion of at least one of the plurality of electrodes; and a position detection module including an electronic control unit configured to determine a co-axial position of the inner elongate member relative to the outer elongate member based on the first signal,
wherein the first sensor member includes a longitudinal center point, wherein the longitudinal center point of the first sensor member is positioned at a longitudinal location equal to a longitudinal center of one of the plurality of electrodes.

2. The apparatus of claim 1, wherein the first sensor member comprises a rectangular strip including a longer side aligned with or offset from a longitudinal axis of the inner elongate member.

3. The apparatus of claim 1, wherein the inner elongate member further includes a second sensor member having a second length different from the first length, the second sensor member configured to generate a second signal indicative of movement of the inner elongate member relative to the outer elongate member, wherein the outer elongate member includes a sensor, wherein the first signal and the second signal are generated in the sensor; and
wherein the electronic control unit is further configured to determine the position of the inner elongate relative to the outer elongate member based at least in part on a magnitude of the first signal in the first sensor member and a magnitude of the second signal in the second sensor member.

4. The apparatus of claim 3, wherein the magnitude of the first signal is different than the magnitude of the second signal.

5. The apparatus of claim 4, wherein the first sensor member and the second sensor member are different sizes.

6. The apparatus of claim 1, wherein the first sensor member consists of a magnetically permeable material.

7. A system comprising:
a catheter including a first sensor member and a plurality of electrodes, wherein the first sensor member extends under a portion of at least one of the plurality of electrodes and wherein the first sensor member includes a longitudinal center point, wherein the longitudinal center point of the first sensor member is positioned at a longitudinal location equal to a longitudinal center of one of the plurality of electrodes;
an introducer, wherein the catheter is configured to move within the introducer;
a sensor, wherein the first sensor member generates a first signal indicative of a relative position between the catheter and the introducer in the sensor; and
an electronic control unit electrically coupled to the sensor and operable to do the following:
  (A) receive the first signal from the sensor;
  (B) analyze the first signal to determine the relative position of the catheter within the introducer; and
  (C) generate relative position information for the catheter within the introducer using the analysis of the first signal,
wherein the first signal generated by the first sensor member includes a maximum magnitude when the longitudinal center point of the first sensor member is positioned at the longitudinal location equal to the sensor.

8. The system of claim 7, wherein the catheter includes a second sensor member, wherein the second sensor member generates a second signal indicative of the relative position between the catheter and the introducer, wherein the first signal has a maximum magnitude different than the second signal, wherein the electronic control unit receives the second signal from the sensor and analyzes the second signal to determine the relative position of the catheter, wherein the first sensor member and the second sensor member each include a rectangular strip including a longer side aligned with or offset from a longitudinal axis of the introducer.

9. The system of claim 8, wherein the first sensor member defines a first length, and the second sensor member defines a second length different from the first length.

10. The system of claim 8, wherein the first sensor member and the second sensor member include a magnetically permeable material.

11. The system of claim 7, wherein the plurality of electrodes are located at a known distance from the first sensor member.

* * * * *